US011976310B2

(12) United States Patent
Bar-Even et al.

(10) Patent No.: US 11,976,310 B2
(45) Date of Patent: May 7, 2024

(54) METHOD FOR THE INCORPORATION OF FORMALDEHYDE INTO BIOMASS

(71) Applicants: SCIENTIST OF FORTUNE S.A., Luxembourg (LU); MAX-PLANCK-GESELLSCHAFT ZUR FÖRDERUNG DER WISSENSCHAFTEN E.V., Munich (DE)

(72) Inventors: Arren Bar-Even; Hai He, Marburg (DE); Philippe Marliere, Luxembourg (LU)

( * ) Notice: Subject to any disclaimer, the term of this patent is extended or adjusted under 35 U.S.C. 154(b) by 0 days.

(21) Appl. No.: 17/800,484

(22) PCT Filed: Feb. 16, 2021

(86) PCT No.: PCT/EP2021/053715
§ 371 (c)(1),
(2) Date: Oct. 7, 2022

(87) PCT Pub. No.: WO2021/165229
PCT Pub. Date: Aug. 26, 2021

(65) Prior Publication Data
US 2023/0212622 A1 Jul. 6, 2023

(30) Foreign Application Priority Data
Feb. 17, 2020 (EP) .................... 20157768

(51) Int. Cl.
C12P 13/04 (2006.01)
C12N 15/52 (2006.01)
C12N 15/70 (2006.01)

(52) U.S. Cl.
CPC .............. *C12P 13/04* (2013.01); *C12N 15/52* (2013.01); *C12N 15/70* (2013.01); *C12Y 101/01103* (2013.01); *C12Y 101/03013* (2013.01); *C12Y 203/01029* (2013.01); *C12Y 401/02* (2013.01); *C12Y 403/01* (2013.01); *C12N 2800/101* (2013.01)

(58) Field of Classification Search
CPC .. C12P 13/04; C12P 7/24; C12P 19/32; C12N 15/52; C12N 15/70; C12N 2800/101; C12N 1/20; C12N 1/205; C12N 9/0006; C12N 9/0016; C12N 9/1029; C12N 9/1096; C12N 9/1205; C12N 9/88; C12N 1/32; C12Y 101/01103; C12Y 101/03013; C12Y 203/01029; C12Y 401/02; C12Y 403/01; C12R 2001/19
See application file for complete search history.

(56) References Cited

PUBLICATIONS

Wang et al. An aldolase-catalyzed new metabolic pathway for the assimilation of formaldehyde and methanol to synthesize 2-Keto-4 hydroxybutyrate and 1,3-Propanediol in *Escherichia coli*. ACS Synth. Biol. 2019, 8, 2483-2493 (Year: 2019).*
Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
International Preliminary Report on Patentability (IPRP) for IA No. PCT/EP2021/053715, dated Sep. 1, 2022.
Yu. H. & Liao, J.C., "A modified serine cycle in *Escherichia coli* coverts methanol and CO2 to two-carbon compounds", Nature Communications,vol. 9, No. 1, Sep. 28, 2018 (Sep. 28, 2018), p. 1-10, DOI: 10.1038/s41467-018-06496-4.
Hernandez, K. et al., "Combining Aldolases and Transaminases for the Synthesis of 2-Amino-4-hydroxybutanoic Acid", ACS Catalysis, vol. 7, No. 3, Feb. 3, 2017 (Feb. 3, 2017), p. 1707-1711, DOI: 10.1021/acscatal.6b03181.
Shames, S.L. & Wedler, F.C., "Homoserine kinase of *Escherichia coli*: Kinetic mechanism and inhibition by I-aspartate semialdehyde", Archives of Biochemistry and Biophysics, vol. 235, No. 2, Dec. 1984 (Dec. 1984), p. 359-370, DOI: 10.1016/0003-9861(84)90209-1.
Laber, B. et al., "Mechanisms of Interaction of *Escherichia coli* Threonine Synthase with Substrates and Inhibitors", Biochemistry,vol. 33, Jan. 1994 (Jan. 1994), p. 3413-3423, DOI: 10.1021/BI00177A035.
Contestabile, R. et al., "L-Threonine aldolase, serine hydroxymethyltransferase and fungal alanine racemase. A subgroup of strictly related enzymes specialized for different functions", vol. 268, Dec. 2001 (Dec. 2001), p. 6508-6525 DOI: 10.1046/j.0014-2956.2001.02606.x.

(Continued)

*Primary Examiner* — Iqbal H Chowdhury
(74) *Attorney, Agent, or Firm* — Perdue IP Law, APC; Donna O. Perdue

(57) ABSTRACT

The present disclosure relates to a method for the incorporation of formaldehyde into biomass comprising the following enzymatically catalyzed steps: (1) condensation of pyruvate with formaldehyde into 4-hydroxy-2-oxobutanoic acid (HOB); (2) amination of the thus produced 4-hydroxy-2-oxobutanoic acid (HOB) to produce homoserine; (3) conversion of thus produced homoserine to threonine; (4) conversion of the thus produced threonine into glycine and acetaldehyde or acetyl-CoA; (5) condensation of the thus produced glycine with formaldehyde to produce serine; and (6) conversion of the thus produced serine to produce pyruvate, wherein said pyruvate can then be used as a substrate in step (1). The disclosure also relates to enzymes for catalyzing the corresponding enzymatic reactions and recombinant microorganisms which express the enzymes for catalyzing the corresponding enzymatic reactions.

Figure 1:
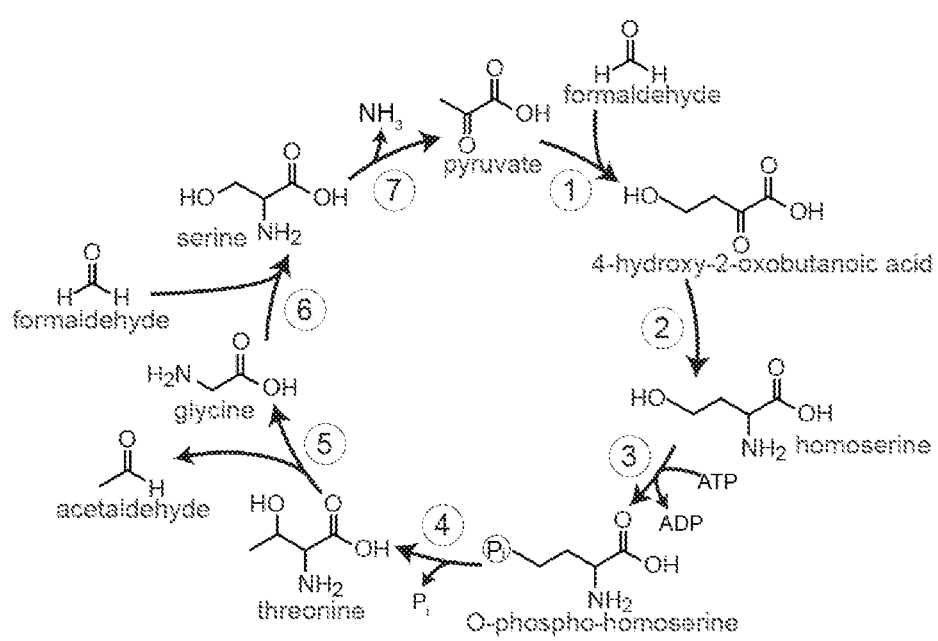

3 Claims, 9 Drawing Sheets
Specification includes a Sequence Listing.

(56) References Cited

PUBLICATIONS

He, H. et al., "An optimized methanol assimilation pathway relying on promiscuous formaldehyde-condensing aldolases in *E. coli*", Metabolic Engineering, vol. 60, Mar. 10, 2020 (Mar. 10, 2020), p. 1-13, DOI: 10.1016/j.ymben.2020.03.002.

International Search Report and Written Opinion (ISR/WO) for PCT/EP2021/053715 dated May 19, 2021.

Extended European Search Report (EESR) for EP 20157768.1 dated Sep. 18, 2020.

* cited by examiner

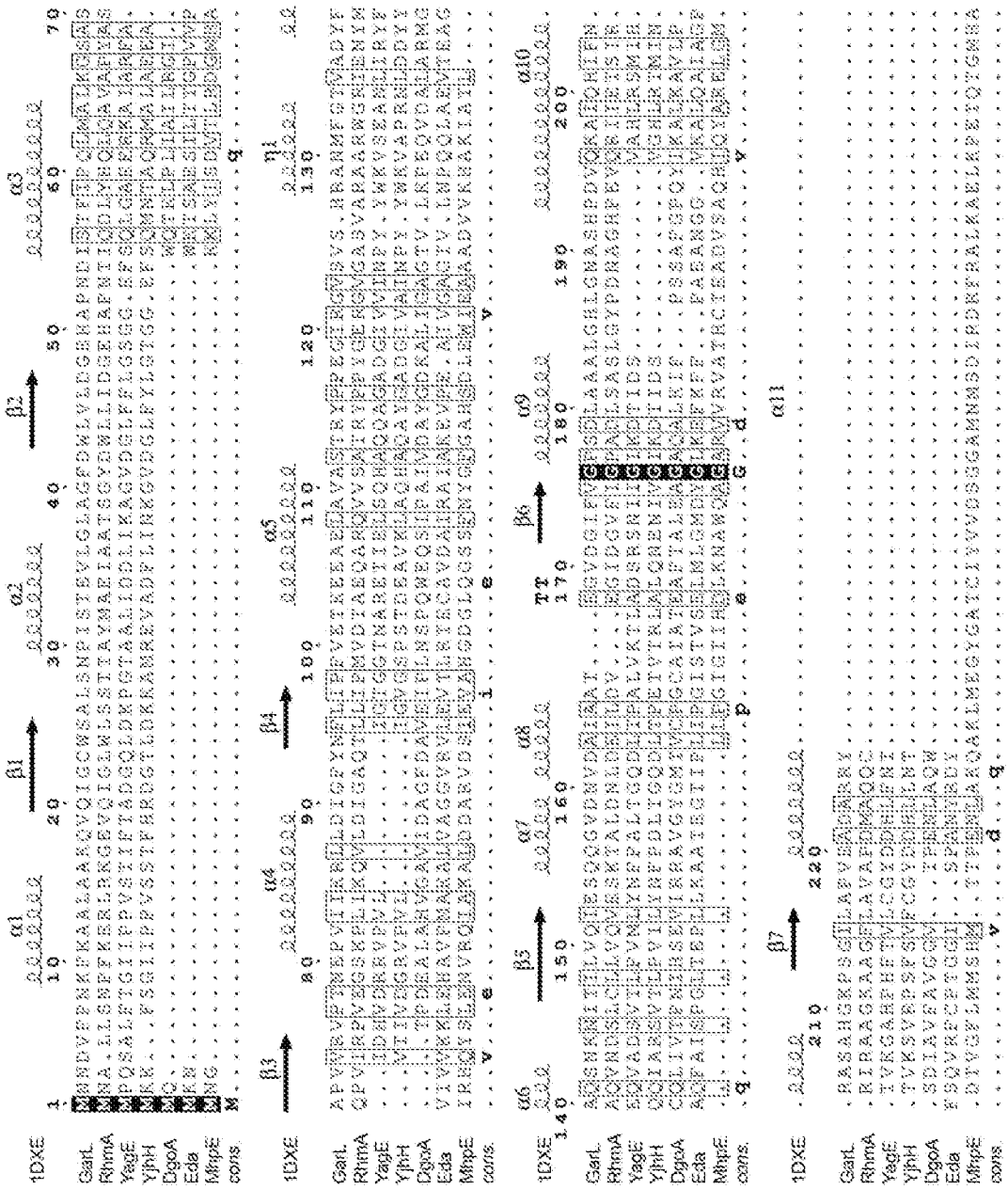
Figure 6.1

Figure 6.2
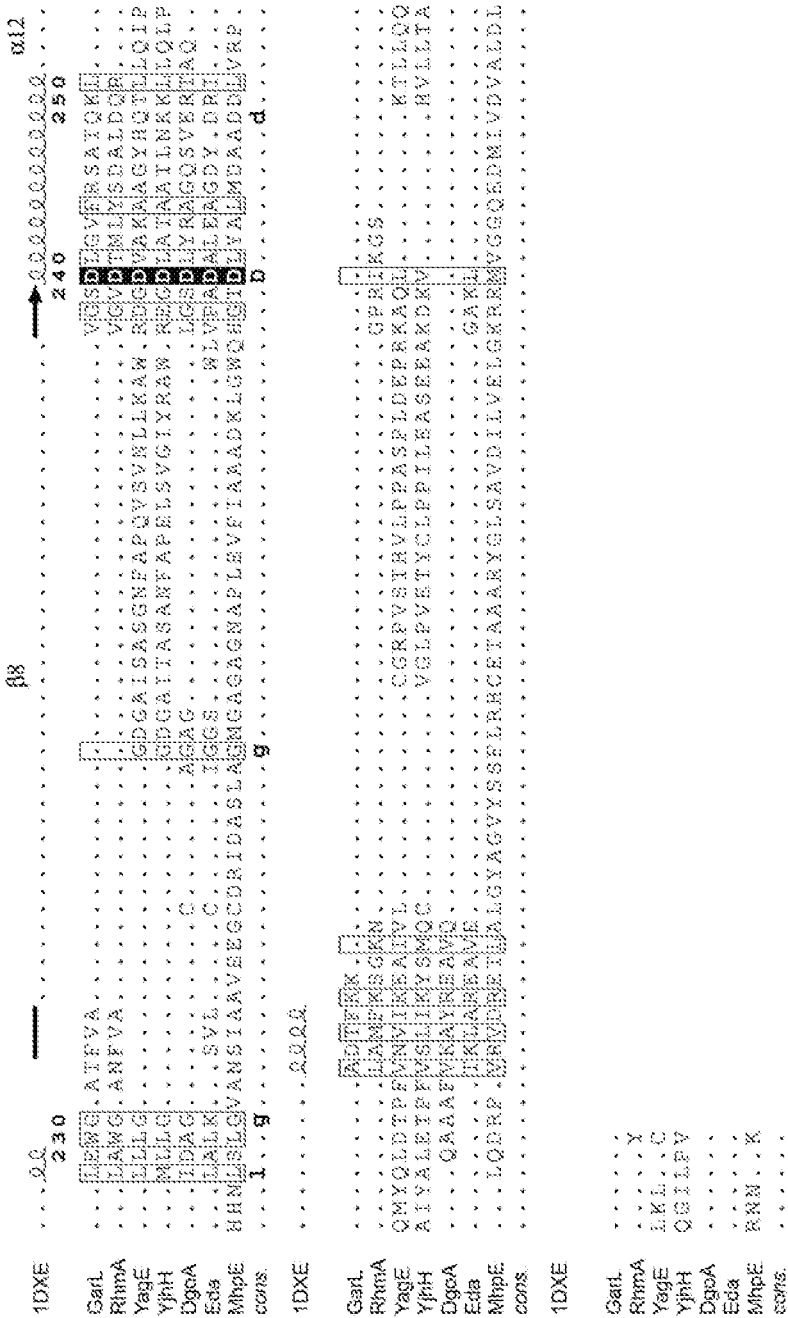

Figure 7
GarL-RhmA
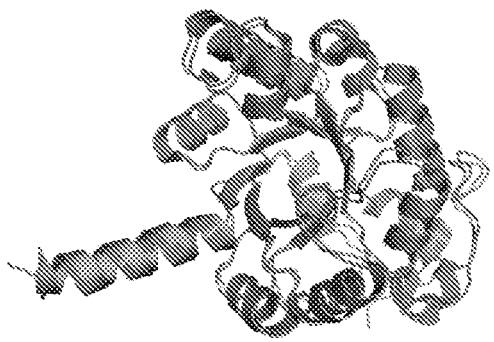
GarL-YagE
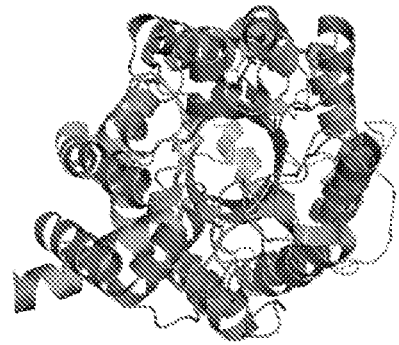
GarL-DgoA
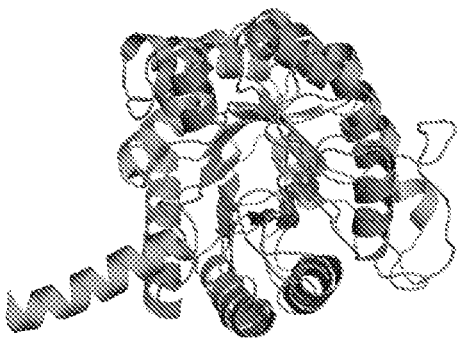
GarL-Eda
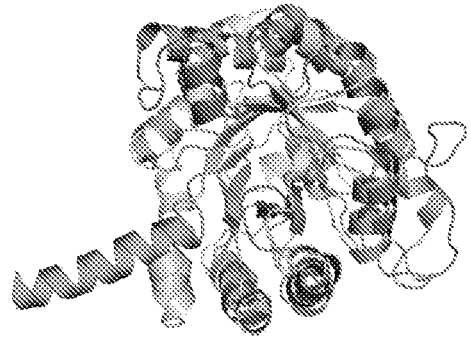
DgoA-Eda
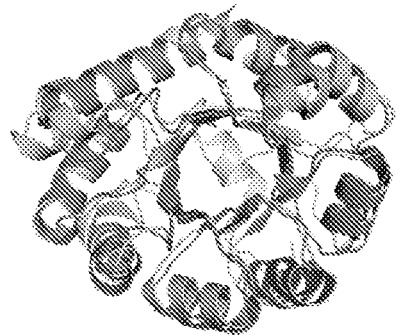
| TM-score / RMSD (Å) | GarL | RhmA | YagE | DgoA | Eda |
|---|---|---|---|---|---|
| GarL (1dxf) | | 0.9713 | 0.5448 | 0.7012 | 0.6853 |
| RhmA (2vwt) | 1.07 | | 0.5354 | 0.6991 | 0.6864 |
| YagE (4ptn) | 2.84 | 3.19 | | 0.7722 | 0.7197 |
| DgoA (2v82) | 3.23 | 3.24 | 2.48 | | 0.8404 |
| Eda (1eua) | 3.36 | 3.47 | 2.73 | 1.81 | |

METHOD FOR THE INCORPORATION OF FORMALDEHYDE INTO BIOMASS

The present invention relates to a method or enzymatic pathway comprising the following enzymatically catalyzed steps
(1) condensation of pyruvate with formaldehyde into 4-hydroxy-2-oxobutanoic acid (HOB);
(2) amination of the thus produced 4-hydroxy-2-oxobutanoic acid (HOB) to produce homoserine;
(3) conversion of thus produced homoserine to threonine;
(4) conversion of the thus produced threonine into glycine and acetaldehyde or acetyl-CoA;
(5) condensation of the thus produced glycine with formaldehyde to produce serine; and
(6) conversion of the thus produced serine to produce pyruvate, wherein said pyruvate can then be used as a substrate in step (1).

This method/pathway allows for the efficient incorporation of formaldehyde into carbon compounds and thus of the conversion of formaldehyde into biomass. The present invention also relates to recombinant microorganisms which express the enzymes for catalyzing the corresponding enzymatic reactions.

Microbial production of commodity chemicals is limited by feedstock availability and cost. Sugars and starches, despite being commonly used, are not ideal microbial feedstocks as their biotechnological utilization directly competes with human consumption, thus eroding food security (Walker, J. Appl. Phycol. 21 (2009), 509-517). Furthermore, the expansion of agricultural cultivation comes at the expense of shrinking natural habitats, hence threatening biodiversity (Scholes et al., in Intergovernmental Science—Policy Platform on Biodiversity and Ecosystem Services (Bonn, Germany; 2018)). The use of lignocellulosic biomass, while avoiding some of these problems, presents other challenges, including heterogenic composition, difficult processing, and deleterious waste products (Sanderson, Nature 474 (2011), 12-14). One carbon compounds provide a favorable alternative as they can be produced at high levels without burdening agricultural production and they represent homogenous, easy-to-handle microbial feedstocks (Takors et al., Microb. Biotechnol. 11 (2018), 606-625; Yishei et al., Curr. Opin. Chem. Biol. 35 (2016), 1-9; Schrader et al., Trends Biotechnol. 27 (2009), 107-115). Methanol is especially interesting as it is completely water miscible, avoiding mass transfer barriers that constrain the use of gaseous one carbon compounds (e.g., carbon monoxide and methane). Methanol can be produced at low-cost from natural gas (Zakaria and Kamarudin, Renew. Sust. Energ. Rev. 65 (2016), 250-261), or it can be produced sustainably and efficiently from $CO_2$ and electrochemically derived hydrogen (Szima and Cormos, J. $CO_2$ Util. 24 (2018), 555-663). Methanol bio-assimilation mostly involves its oxidation to formaldehyde, followed by formaldehyde incorporation into biomass via a dedicated cycle.

There has been much recent progress in the metabolic engineering of microorganisms that naturally grow on methanol, e.g., *Methylobacterium extorquens* (Schada von Borzyskowski et al., ACS Synthetic Biology 4 (2015), 430-443; Marx and Lidstrom, Microbiology 150 (2004), 9-19). Also multiple recent efforts have sought to engineer biotechnological hosts for growth on methanol via one of the naturally occurring methanol assimilation pathways (Whitaker, Curr. Opin. Biotechnol. 33 (2015), 165-175; Zhang et al., RSC Advances 7, (2017) 4083-4091): the ribulose monophosphate (RuMP) cycle (Chen et al., Metab. Eng. 49, (2018) 257-266; Meyer et al., Nature Communications 9, (2018) 1508; He et al., ACS Synthetic Biology 7, (2018) 1601-1611), the dihydroxyacetone (DHA) cycle (Dai et al., Bioresour. Technol. 245 (2017), 1407-1412) and the swine cycle (Yu and Liao, Nature Communications 9 (2018), 3992). However, these natural pathways might not represent optimal solutions. Better pathways, more efficient in the use of cellular resources and/or more metabolically compatible with the host microorganism, could be designed and implemented. For example, a recent study designed and partially implemented a modified serine cycle in *E. coli*, where some of the natural reactions were replaced with others, better fitting the endogenous metabolism of the host (Yu and Liao, Nature Communications 9 (2018), 3992). However, the serine cycle and its modified variants are ATP-inefficient, which results in low biomass and product yields (Claassens et al., Nature Catalysis 2 (2019), 437). In other studies, a new-to-nature formolase reaction was demonstrated, where two or three formaldehyde molecules are condensed to generate glycolaldehyde or DHA, respectively (Lu et al., Nature Communications 10 (2019), 1378; Wang et al., Bioresour. Bioprocess. 4 (2017), 41). However, the condensation rate and affinity for formaldehyde are too low to be physiologically relevant.

Thus, there is a need to develop means and methods which allow for the efficient assimilation and incorporation of formaldehyde (which may be produced from methanol) into biomass thereby facilitating the use of, e.g., methanol as a feedstock for bioproduction.

The present invention meats this demand by providing a method or enzymatic pathway comprising the following enzymatically catalyzed steps
(1) condensation of pyruvate with formaldehyde into 4-hydroxy-2-oxobutanoic acid (HOB);
(2) amination of the thus produced 4-hydroxy-2-oxobutanoic acid (HOB) to produce homoserine;
(3) conversion of thus produced homoserine to threonine;
(4) conversion of the thus produced threonine into glycine and acetaldehyde or actyl-CoA;
(5) condensation of the thus produced glycine with formaldehyde to produce serine; and
(6) conversion of the thus produced serine to produce pyruvate, wherein said pyruvate can then be used as a substrate in step (1).

This method/pathway allows for the efficient incorporation of formaldehyde into carbon compounds and thus its conversion into biomass.

The above specified sequence of enzymatic steps represents a cycle (in the following also referred to as the "homoserine cycle"), a non-limiting example of which is shown in FIG. 1. The inventors in their effort to provide more efficient means for formaldehyde assimilation started out from the above-mentioned swine cycle and provided an improved variant thereof which allows for a more efficient incorporation of formaldehyde. The provided pathway also has the advantage that it can easily be implemented in microorganisms which are frequently used for biotechnological production methods, such as *E. coli*.

In the homoserine cycle, pyruvate is condensed with formaldehyde to generate the non-natural metabolite 4-hydroxy-2-oxobutanoate (HOB) (Bouzon et al., ACS Synthetic Biology 6 (2017), 1520-1533), which is subsequently aminated to homoserine. The first of these reactions—item (1) in FIG. 1)—was found to be promiscuously catalyzed by *E. coli* 2-keto-3-deoxy-L-rhamnonate aldolase (RhmA) (Hernandez et al., ACS Catal. 7 (2017), 1707-1711). The latter reaction—HOB amination (item (2) in FIG. 1)—is supported by numerous aminotransferases (Hernandez et al., ACS Catal. 7 (2017), 1707-1711; Walther et al., Metab. Eng. 45 (2018), 237-245; Zhong et al., ACS Synthetic Biology 8 (2019), 587-595) as well as amino acid dehydrogenases such as (engineered) glutamate dehydrogenase (Chen et al., Biotechnol. J. 10 (2015), 284-289). While the literature mostly reports the reaction in the reverse direction, it can also be used in the direction of HOB amination since it is reversible. This route effectively replaces a carboxylation reaction (by phosphoenolpyruvate carboxylase) with a formaldehyde assimilation reaction that provides an alternative way to generate a $C_4$ Intermediate. Homoserine is then converted into threonine, e.g. by the action of homoserine kinase (ThrB, item (3) in FIG. 1) and threonine synthase (ThrC, item (4) in FIG. 1). Threonine is cleaved to produce glycine and acetaldehyde. This can, e.g., be achieved by making use of a threonine aldolase (item (5) in FIG. 1, for example by the same threonine aldolase (LtaE) that catalyzes the SAL reaction (item (6) in FIG. 1) to regenerate glycine and produce acetaldehyde. The produced acetaldehyde can, e.g., be further oxidized to acetyl-CoA and assimilated to central metabolism.

In the homoserine cycle, the glycine produced by the cleavage of threonine is directly condensed with formaldehyde to generate serine. This reaction (item (6) in FIG. 1) (herein also referred to as the serine aldolase (SAL) reaction) was previously found to be promiscuously catalyzed (in vitro) by a threonine aldolase (LtaE) (Contestabile et al., Eur. J. Biochem. 268 (2001). 6506-6525). The SAL reaction bypasses the known very long, multi-cofactor-dependent, and ATP-inefficient route for formaldehyde assimilation to 5,10-methylene-tetrahydrofolate ($CH_2$-THF) (Crowther et al., J. Bacteriol. 190 (2008), 5057-5082). As within the previously proposed modified serine cycles (Yu and Lao, Nature Communications 9 (2018), 3992; Bar-Even, Biochemistry 55 (2016), 3851-3863), serine is then deaminated to pyruvate by serine deaminase (item (7) in FIG. 1), bypassing a longer route via glycerate, which further involves the highly toxic intermediate hydroxypyruvate (Kim and Copley, Proc. Natl. Acad. Sci. USA 109 (2012), E2856-2854). The resulting pyruvate can then be used in step (1) of the method thereby closing the cycle.

It is shown that this newly proposed synthetic route can outperform the serine cycle and its known variants with respect to biomass yield, thermodynamic favorability, and implementation into host endogenous metabolism.

The inventors could also demonstrate the in vivo activity of the cycle and, in particular, the functionality of those reactions of the pathway which rely on non-natural reactions. More precisely, the inventors demonstrated by way of experiments the in vivo activity of different pathway segments including all the required actives, in particular also the promiscuous enzyme activities which can be provided by a host cell itself without the need to have it genetically modified to express these enzyme activities. The cycle can efficiently provide building blocks which are essential for the production of biomass. The data provided in the present application confirm that the proposed pathway will allow the efficient assimilation of methanol (via formaldehyde) and, thus, the implementation of a highly efficient conversion of this one carbon feedstock into commodity chemicals.

The method according to the present invention differs from the known serine cycle, e.g., in that it replaces $CO_2$ fixation with formaldehyde assimilation. For this purpose, it relies on two formaldehyde-condensing reactions which are catalyzed (promiscuously) by aldolases.

As indicated above, the method or pathway according to the present invention allows for the incorporation of formaldehyde. The term "incorporation of formaldehyde" means that formaldehyde is assimilated into carbon compounds that ae part of microbial central metabolism and can, thus, be converted into biomass and/or desired compounds. Thus, the method/pathway can be used for the assimilation of formaldehyde into carbon compounds and its incorporation into biomass.

Step 1 of the Method: Condensation of Pyruvate with Formaldehyde so as to Produce 4-Hydroxy-2-Oxobutanoic Acid (HOB)

In a first step of the method/pathway, pyruvate is condensed in an enzymatically catalyzed reaction with formaldehyde so as to produce 4-hydroxy-2-oxobutanoic acid (HOB).

In a preferred embodiment, this condensation is achieved by making use of an aldolase and more preferably of an aldolase which is classified in EC 4.1.2._.

Examples of aldolases classified in EC 4.1.2._ which may be particularly useful in the context of the method/pathway of the present invention are aldolases selected from the following:

(i) aldolases classified in EC 4.1.2.53 (2-keto-3-deoxy-L-rhamnonate aldolase);
(ii) aldolases classified in EC 4.1.251 (2-dehydro-3-deoxy-D-gluconate aldolase);
(iii) aldolases classified in EC 4.1.2.28 (2-dehydro-3-deoxy-D-pentonate aldolase);
(iv) aldolases classified in EC 4.1.2.20 (2-dehydro-3-deoxyglucarate aldolase).

In one preferred embodiment, the aldolase is an aldolase which belongs to the HpcH aldolase family. Aldolases classified as belonging to the HpcH aldolase family are characterized in that they domain referred to as "HpcH" (Pfam family PF03328; pfam.xfam.org/family/PF03328). Moreover, such aldolases are preferably characterized in using a catalytic mechanism which involves a divalent metal cation for donor binding and enolization. Examples for such aldolases are the aldolases classified as EC 4.1.2.53 or classified as EC 4.1.2.20.

In another embodiment, the aldolase is an aldolase which belongs to the DHDPS aldolase family. Aldolases classified as belonging to the DHDPS aldolase family are characterized in that they domain referred to as "DHDPS" (Pfam family PF00701, pfam.xfam.org/family/PF00701). Moreover, such aldolases are preferably characterized in using a catalytic mechanism which involves a catalytic lysine residue to form a Schiff base with the donor substrate. Examples for such aldolases are the aldolases classified as EC 4.1.2.5 or classified as EC 4.1.2.28.

The condensation of pyruvate with formaldehyde into 4-hydroxy-2-oxobutanoic acid (HOB) is a reaction which is not known to occur naturally. However, there was a report in the literature (Hernandez et al., ACS Catal. 7 (2017), 1707-1711) that an aldols from *E. coli*, i.e. the RhmA/YfaU (EC 4.1.2.53) protein, can promiscuously catalyze this conversion. Moreover, the inventors could show that this conversion can actually be catalyzed by various aldolases in a promiscuous manner, i.e. these enzymes can use pyruvate and formaldehyde as substrates although their natural substrates are different from these compounds. Moreover, as is evident from the appended Examples, the inventors could also show that corresponding aldolases are capable of catalyzing the corresponding reaction in vivo and to an extent which leads to an efficient condensation of pyruvate and formaldehyde into 4-hydroxy-2-oxobutanoic acid (HOB).

Aldolases classified in EC 4.1.2.53 (2-keto-3-deoxy-L-rhamnonate aldolase) naturally catalyze the reaction

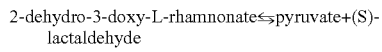
2-dehydro-3-doxy-L-rhamnonate⇌pyruvate+(S)-lactaldehyde i.e. the reversible retro-aldo cleavage of 2-dehydro-3-decy-L-rhamnonate to pyruvate and (S)-lactaldehyde (Rakus et al., Biochemistry 47 (2008), 9944-9954; Read et al., Biochemistry 47 (2008), 9955-9985).

This enzyme has been identified in several organisms, e.g. in *Azotobacter vinelandii*, in *Scheffersomyces stipitis* and *Schwanniomyces polymorphus* as well as in *E. coli* (Uniprot accession numbers: P76489 and D30KU2). In principle any 2-keto-3-deoxy-L-rhamnonate aldolase (EC 4.1.2.53) can be employed in the method according to the present invention as long as it can catalyze the condensation of pyruvate with formaldehyde into 4-hydroxy-2-oxobutanoic acid (HOB). In a preferred embodiment an enzyme from *E. coli* is used, in particular an enzyme encoded by the rhmA gene of *E. coli* or by the yfaU gene of *E. coli* (Hernandez et al., ACS Catal. 7 (2017), 1707-1711).

In a preferred embodiment such an enzyme has an amino acid sequence as shown in SEQ ID NO: 1 or shows an amino acid sequence which is at least x % homologous to SEQ ID NO: 1 and has the activity of a 2-keto-3-doxy-L-rhamnonate aldolase (EC 4.1.2.53) with x being an integer between 60 and 100, preferably 65, 70, 75, 80, 85, 90, 91, 92, 93, 94, 95, 96, 97, 98 or 99 wherein such an enzyme is capable of catalyzing the condensation of pyruvate with formaldehyde into 4-hydroxy-2-oxobutanoic acid (HOB).

Preferably, the degree of identity is determined by comparing the respective sequence with the amino acid sequence of SEQ ID NO: 1.

As regards the determination of sequence identity as described in the present application, generally the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined by performing pairwise alignment using preferably algorithms and software well known in the art, such as Needleman-Wunsch algorithm with the EMBOSS NEEDLE software.

When applying this methodology to determine whether a particular sequence is, for instance, at least 60% identical to a reference sequence default settings of the EMBOSS NEEDLE software may be used, which are defined as follows:

Matrix: BLOSUM62
Gap open: 10
Gap extend: 0.5
No end gap penalty.

Preferably, the degree of identity is calculated over the complete length of the aligned sequence.

Aldolases classified in EC 4.1.2.51 (2-dehydro-3-deoxy-D-gluconate aldolase) naturally catalyze the reaction

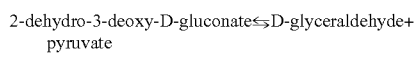
2-dehydro-3-deoxy-D-gluconate⇌D-glyceraldehyde+pyruvate i.e. the formation of 2-keto-3-deoxy-gluconate (KDG) from pyruvate and glyceraldehyde (Bhaskar al., Proteins 79 (2011), 1132-1142), or the reaction (Liu et al., Appl. Microbiol. Biotechnol 97 (2013), 3409-3417):

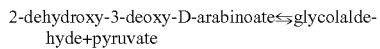
2-dehydroxy-3-deoxy-D-arabinoate⇌glycolaldehyde+pyruvate

The enzyme has, e.g., been identified in *Picrophilus torridus* and in *E. coli*. In principle any 2-dehydro-3-deoxy-D-gluconate aldolase (EC 4.1.2.51) can be employed in the method according to the present invention as long as it can catalyze the condensation of pyruvate with formaldehyde into 4-hydroxy-2-oxobutanoic acid (HOB). In a preferred embodiment an enzyme from *E. coli* is used, in particular an enzyme encoded by the yagE gene of *E. coli* (Uniprot accession number P75682). In a preferred embodiment such an enzyme has an amino acid sequence as shown in SEQ ID NO: 2 or shows an amino acid sequence which is at least x % homologous to SEQ ID NO: 2 and has the activity of a 2-dehydro-3-deoxy-D-gluconate aldolase (EC 4.1.2.51) with x being an integer between 60 and 100, preferably 65, 70, 75, 80, 85, 90, 91, 92, 93, 94, 95, 96, 97, 98 or 99 wherein such an enzyme is capable of catalyzing the condensation of pyruvate with formaldehyde into 4-hydroxy-2-oxobutanoic acid (HOB).

Preferably, the degree of identity is determined by comparing the respective sequence with the amino acid sequence of SEQ ID NO: 2. As regards the determination of the degree of sequence identity the same applies as had been set forth above.

Aldolases classified in EC 4.1.2.28 (2-dehydro-3-deoxy-D-pentonate aldolase) naturally catalyze the reaction (Liu et al., Appl. Microbiol. Biotechnol 97 (2013), 3409-3417):

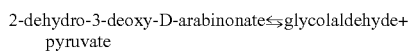
2-dehydro-3-deoxy-D-arabinonate⇌glycolaldehyde+pyruvate

The enzyme has, e.g., been identified in *Pseudomonas* sp. (Dahms, A. S.; Biochem. Biophys. Res. Commun. 60, 1433-1439 (1974)) and in *E. coli* (Uniprot accession number: P39359). In principle any 2-dehydro-3-deoxy-D-pentonate aldolase (EC 4.1.2.28) can be employed in the method according to the present invention as long as it can catalyze the condensation of pyruvate with formaldehyde into 4-hydroxy-2-oxobutanoic acid (HOB). In a preferred embodiment an enzyme from E cci is used, in particular an enzyme encoded by the yjhH gene of *E. coli* (Liu et al., loc cit.; Uniprot accession number: P39359).

In a preferred embodiment such an enzyme has an amino acid sequence as shown in SEQ ID NO: 3 or shows an amino acid sequence which is at least x % homologous to SEQ ID NO: 3 and has the activity of a 2-dehydro-3-deoxy-D-pentonate aldolase (EC 4.1.2.28) with x being an integer between 60 and 100, preferably 65, 70, 75, 80, 85, 90, 91, 92, 93, 94, 95, 98, 97, 98 or 99 wherein such an enzyme is capable of catalyzing the condensation of pyruvate with formaldehyde into 4-hydroxy-2-oxobutanoic acid (HOB).

Preferably, the degree of identity is determined by comparing the respective sequence with the amino acid sequence of SEQ ID NO: 3. As regards the determination of the degree of sequence identity the same applies as had been set forth above.

Aldolases classified in EC 4.1.2.20 (2-dehydro-3-deoxy-glucarate aldolase) naturally catalyze the reaction

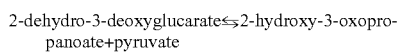
2-dehydro-3-deoxyglucarate⇌2-hydroxy-3-oxopropanoate+pyruvate as, e.g., described in Hubbard et al., Biochemistry 37 (1998), 14369-14375).

This enzyme has been identified in several organisms, e.g. in *Klebsiella aerogenes, Leptospira interrogans, Picrophilus torridus* and in *E. coli* (Uniprot accession number P23522). In principle any 2-dehydro-3-deoxyglucarate aldolase (EC 4.1.2.20) can be employed in the method according to the present invention as long as it can catalyze the condensation of pyruvate with formaldehyde into 4-hydroxy-2-oxobutanoic acid (HOB). In a preferred embodiment an enzyme from *E. coli* is used, in particular an enzyme encoded by the garL gene of *E. coli* (Uniprot accession number P23522). In a preferred embodiment such an enzyme has an amino acid sequence as shown in SEQ ID NO: 4 or shows an amino acid sequence which is at least x % homologous to SEQ ID NO: 4 and has the activity of a 2-dehydro-3-deoxyglucarate aldolase (EC 4.1.2.20) with x being an integer between 60 and 100, preferably 65, 70, 75, 80, 85, 90, 91, 92, 93, 94, 95, 98, 97, 98 or 99 wherein such an enzyme is capable of catalyzing the condensation of pyruvate with formaldehyde into 4-hydroxy-2-oxobutanoic acid (HOB).

Preferably, the degree of identity is determined by comparing the respective sequence with the amino acid sequence of SEQ ID NO: 4. As regards the determination of the degree of sequence identity the same applies as had been set forth above.

Step 2 of the Method: Conversion of 4-Hydroxy-2-Oxobutanoic Acid (HOB) into Homoserine According to the method/pathway of the present invention, the 4-hydroxy-2-oxobutanoic acid (HOB) produced in step (1) is further enzymatically converted in step (2) into homoserine by an amination reaction.

It is known that in nature three different enzyme families can convert an amino acid to the corresponding α-keto acid (or the reversible reaction), namely: (1) amino acid transaminase (aminotransferases), (2) amino acid dehydrogenase; and (3) amino acid deaminase (oxidase). In the method of the present invention, in principle enzymes from any one of these groups can be employed for catalyzing the conversion of HOB into homoserine. Since basically all organisms, including all microorganisms, express enzymes of the above-mentioned three groups, the method of the present invention, when implemented in vivo in an organisms can rely on endogenously occurring enzyme activities of any of the above-mentioned three groups for achieving the conversion of HOB into homoserine.

The amination can preferably be achieved by an aminotransferase enzyme or by an amino acid dehydrogenase enzyme. In a preferred embodiment, the amination is achieved by making use of an aminotransferase classified in EC 2.6.1._ or by an amino acid dehydrogenase classified in EC 1.4.1._. In particular, it has been reported in the literature that this reaction (in most reports in the reverse direction) is supported by numerous aminotransferases (se, e.g., Bouzon et al., ACS Synth. Biol. 6 (2017), 1520-1533; Hernandez et al., ACS Catal. 7 (2017), 1707-1711; Walther et al., Metab. Eng. 45 (2018), 237-245; Zhong et al., ACS Synthetic Biology 8 (2019), 587-595) as well as amino acid dehydrogenases such as (engineered) glutamate dehydrogenase (Chen et al., Biotechnol. J. 10 (2015), 284-289).

The use of an aminotransferase classified in EC 2.6.1._ for carrying out the conversion of HOB into homoserine has already been described in the literature, e.g. in Bouzon et al. (ACS Synth. Biol. 6 (2017), 1520-1533).

Examples of aminotransferases classified in EC 2.6.1._ which may be particularly useful in the context of the method/pathway of the present invention are aminotransferases selected from the following:

(i) aminotransferases classified in EC 2.8.1.2 (glutamate-pyruvate aminotransferase; also referred to alanine transaminase);
(ii) aminotransferases classified in EC 2.6.1.1 (aspartate aminotransferase; also referred to as aspartate transaminase);
(iii) aminotransferases classified in EC 2.6.1.42 (branched-chain amino acid aminotransferase).

Aminotransferases classified in EC 2.6.1.2 (glutamate-pyruvate aminotransferase; also referred to as alanine transaminase) naturally catalyze the reaction:

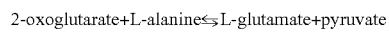
2-oxoglutarate+L-alanine⇌L-glutamate+pyruvate

This enzyme occurs in a large variety of organism, including eukaryotic and prokaryotic organisms, such as animals, plants, fungi and bacteria. In principle any glutamate-pyruvate aminotransferase (EC 2.8.1.2) can be employed in the method according to the present invention as long as it can convert HOB into homoserine. In a preferred embodiment an enzyme from *E. coli* is used, in particular an enzyme encoded by the alaC and alaA genes of *E. coli* (Uniprot accession numbers P77434 and P0A959). Bouzon et al. (ACS Synth. Biol. 6 (2017), 1520-1533) already described the use of a glutamate-pyruvate aminotransferase (EC 2.6.1.2) for the reversible conversion of L-homoserine and 2-oxoglutarate into HOB and L-glutamate. The enzyme from *E. coli* employed in Bouzon et al. (ACS Synth. Biol. 6 (2017), 1520-1533) showed substitutions at positions 142 and 275, namely the substitutions A142P and Y275O, which increase the catalytic efficiency of the enzyme for homoserine dramatically. Thus, in a preferred embodiment, a glutamate-pyruvate aminotransferase (EC 2.6.1.2) is employed which shows substitutions at position 142 and/or 275 in the sequence of the *E. coli* AlaC protein or at positions corresponding to these positions and even more preferably substitutions from A to P at position 142 (or a corresponding position) and/or a substitution from Y to D at position 275 (or a corresponding position).

Aminotransferases classified in EC 2.6.1.1 (aspartate aminotransferase; also referred to as aspartate transaminase) naturally catalyze the reaction:

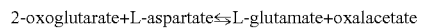
2-oxoglutarate+L-aspartate⇌L-glutamate+oxalacetate

This enzyme occurs in a large variety of organism, including eukaryotic and prokaryotic organisms, such as animals, plants, fungi and bacteria. In principle any aspartate aminotransferase (EC 2.6.1.1) can be employed in the method according to the present invention as long as it can convert HOB into homoserine. In a preferred embodiment an enzyme from *E. coli* is used, in particular an enzyme encoded by the aspC gene of *E. coli* (Uniprot accession number P00509). For this enzyme it has already been reported that it can catalyze this reaction (Walther et al, Metabolic Engin. 45 (2018), 237-245; Zhong et al., ACS Synthetic Biology 8 (2019) 587-95).

Aminotransferases classified in EC 2.6.1.42 (branched-chain amino acid aminotransferase) naturally catalyze the reactions:

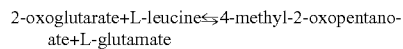
2-oxoglutarate+L-leucine⇌4-methyl-2-oxopentanoate+L-glutamate

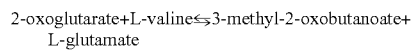
2-oxoglutarate+L-valine⇌3-methyl-2-oxobutanoate+L-glutamate

This enzyme occurs in a large variety of organism, including eukaryotic and prokaryotic organisms, such as animals, plants, fungi and bacteria. In principle any branched-chain amino acid aminotransferase (EC 2.6.1.42) can be employed in the method according to the present invention as long as it can convert HOB into homoserine. In a preferred embodiment an enzyme from *E. coli* is used, in particular an enzyme encoded by the ilvE gene of *E. coli* (Uniprot accession number P0AB80). For this enzyme it has already been reported that it can catalyze this reaction (Walther at al, Metabolic Engin. 45 (2018), 237-245).

The use of an amino acid dehydrogenase classified in EC 1.4.1._ for carrying out the conversion of HOB into homoserine has also already been described in the literature, e.g. in Chen et al. (Biotechnol. J. 10 (2015), 284-289). Examples of amino acid dehydrogenases classified in EC 1.4.1._ which may be particularly useful in the context of the method/pathway of the present invention are amino acid dehydrogenases classified in EC 1.4.1.4 (glutamate dehydrogenase (NADP$^+$)).

Glutamate dehydrogenase (NADP$^+$) (EC 1.4.1.4) naturally catalyzes the reaction:

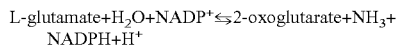

This enzyme occurs in a large variety of organism, including eukaryotic and prokaryotic organisms, such as animals, plants, fungi and bacteria. In principle any glutamate dehydrogenase (NADP$^+$) (EC 1.4.1.4) can be employed in the method according to the present invention as long as it can convert HOB into homoserine. In a preferred embodiment an enzyme from *E. coli* is used, in particular an enzyme encoded by the gdhA gene of *E. coli* (Uniprot accession number P00370).

As reported in Chen et al. (Biotechnol. J. 10 (2015), 284-289), glutamate dehydrogenase (NADP$^+$) (EC 1.4.1.4) can accept homoserine as a substrate albeit with a low activity. However, Chen et al. (loc. cit.) showed that mutants of this enzyme can be provided which show a strongly increased activity using homoserine as a substrate. Thus, in a preferred embodiment, a mutant version of a glutamate dehydrogenase (NADP$^+$) (EC 1.4.1.4) is employed which shows an increased activity in using homoserine as a substrate and, in particular a mutant version as disclosed in Chen et al. (Biotechnol. J. 10 (2015), 284-289).

Step 3 of the Method: Conversion of Homoserine into Threonine

The conversion of the homoserine produced in step (2) into threonine according to step (3) of the method according to the present invention can be achieved by methods known to the person skilled in the art. In a preferred embodiment, the conversion of the homoserine produced in step (2) into threonine takes place by
(i) phosphorylation of thus produced homoserine to produce o-phosphohomoserine; and
(ii) dephosphorylation of the thus produced o-phosphohomoserine to produce threonine.

These are naturally reactions. The reaction of step (i), i.e. the phosphorylation of homoserine to produce o-phosphohomoserine is catalyzed by enzymes classified in EC 2.7.1.39 (homoserine kinase). The reaction proceeds according to the following scheme:

This enzyme occurs in a large variety of organism, including eukaryotic and prokaryotic organisms, such as plants, fungi and bacteria. In principle any homoserine kinase (EC 2.7.1.39) can be employed in the method according to the present invention as long as it can convert homoserine into o-phosphohomoserine. In a preferred embodiment an enzyme from *E. coli* is used, in particular an enzyme encoded by the thrB gene of *E. coli* (Uniprot accession number P00547).

The reaction of step (i), i.e. the dephosphorylation of the produced o-phosphohomoserine to produce threonine is catalyzed by enzymes classified in EC EC 4.2.3.1 (threonine synthase). The reaction proceeds according to the following scheme:

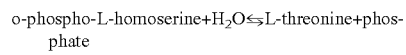

This enzyme occurs in a large variety of organism, including eukaryotic and prokaryotic organisms, such as plants, fungi and bacteria. In principle any threonine synthase (EC 4.23.1) can be employed in the method according to the present invention as long as it can convert o-phosphohomoserine into threonine. In a preferred embodiment an enzyme from *E. coli* is used, in particular an enzyme encoded by the thrC gene of *E. coli* (Uniprot accession number P00934).

Step 4 of the Method: Conversion of Threonine into Glycine and Acetaldehyde

In step (4) of the method according to the present invention threonine is converted into glycine. This conversion can be achieved in different ways.

In one embodiment, threonine is converted into glycine and acetaldehyde. This conversion can, e.g., be achieved by using a threonine aldolase. Threonine aldolases are enzymes which convert threonine (or allo-threonine) into glycine and acetaldehyde. Examples for suitable threonine aldolases are threonine aldolases which are classified in EC 4.1.2.5 or EC 4.1.2.48.

Threonine aldolases classified in EC 4.1.2.5 have been identified in a large variety of organism, including eukaryotic and prokaryotic organisms, such as plants, animals and bacteria. In principle any threonine aldolase classified in EC 4.1.2.5 can be employed in the method according to the present invention as long as it can convert threonine into glycine and acetaldehyde.

Threonine aldolases classified in EC 4.1.2.48 (also referred to as low-specificity L-threonine aldolases) have bean identified in a large variety of organism, including eukaryotic and prokaryotic organisms, such as fungi and bacteria. In principle any threonine aldolase classified in EC 4.1.2.48 can be employed in the method according to the present invention as long as it can convert threonine into glycine and acetaldehyde. In a preferred embodiment an enzyme from *E. coli* is used, in particular an enzyme encoded by the ltaE gene of *E. coli* (Uniprot accession number P75823).

In a preferred embodiment such an enzyme has an amino acid sequence as shown in SEQ ID NO: 5 or shows an amino acid sequence which is at least x % homologous to SEQ ID NO: 3 and has the activity of a low-specificity L-threonine aldolases (EC 4.1.2.48) with x being an integer between 60 and 100, preferably 65, 70, 75, 80, 85, 90, 91, 92, 93, 94, 95, 96, 97, 98 or 99 wherein such an enzyme is capable of catalyzing the conversion of threonine into glycine and acetaldehyde.

Preferably, the degree of identity is determined by comparing the respective sequence with the amino acid sequence of SEQ ID NO: 5. As regards the determination of the degree of sequence identity the same applies as had been set forth above.

In an alternative embodiment, threonine can be converted in step (5) into glycine and acetyl-CoA. This conversion can, e.g., be achieved by a combination of a threonine dehydrogenase (EC 1.1.1.103) and a 2-amino-3-ketobutyrate CoA ligase (EC 2.3.1.29).

Threonine dehydrogenase (EC 1.1.1.103) naturally catalyzes the following reaction:

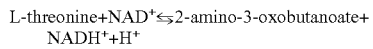

Threonine dehydrogenase classified in EC 1.1.1.103 has been identified in a large variety of organism, including eukaryotic and prokaryotic organisms, such as animals and bacteria. In principle any threonine dehydrogenase classified in EC 1.1.1.103 can be employed in the method according to the present invention as long as it can convert threonine into 2-amino-3-oxobutanoate. In a preferred embodiment an enzyme from $E.\ coli$ is used, in particular an enzyme encoded by the tdh gene of $E.\ coli$ (Uniprot accession number P07913).

2-amino-3-ketobutyrate CoA ligase (EC 2.3.1.29; also referred to as glycine C-acetyltransferase) naturally catalyzes the following reaction:

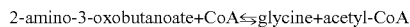

The enzyme has been identified in a large variety of organism, including eukaryotic and prokaryotic organisms, such as animals and bacteria. In principle any 2-amino-3-ketobutyrate CoA ligase classified in EC 2.3.1.29 can be employed in the method according to the present invention as long as it can convert 2-amino-3-oxobutanoate and CoA into glycine and acetyl-CoA. In a preferred embodiment an enzyme from $E.\ coli$ is used, in particular an enzyme encoded by the kbl gene of $E.\ coli$ (Uniprot accession number P0AB77).

Step 5

According to step (5) of the method of the invention, glycine is condensed with formaldehyde so as to produce seine. This condensation reaction can. e.g., be achieved by making use of a threonine aldolase. As regards the definition of threonine aldolase, the same applies as had already been set forth above in connection with step (4) of the method. Thus, in a preferred embodiment the threonine aldolase used in this step is a threonine aldolase which is classified in EC 4.1.2.5 or EC 4.1.2.48. As regards the preferred embodiments, the same applies as has been set forth above in connection with step (4).

In a particularly preferred embodiment, the threonine aldolase employed in this step is a threonine aldolase classified in EC 4.1.2.48, even more preferably a threonine aldolase from $E.\ coli$ (Uniprot accession number P75823) encoded by the latE gene. It has been reported in Contestabile et al (Eur. J. Biochem 268 (2001), 6508-6525) that a threonine aldolase can indeed catalyze this condensation of glycine with formaldehyde so as to produce serine.

Step 6

According to step (6) of the method of the invention, the serine produced in step (5) is then further converted so as to produce pyruvate. Enzymatic reactions for achieving this conversion and the respective enzymes are known to the person skilled in the art. In one embodiment, the conversion of serine into pyruvate is achieved by a deamination reaction. Enzymes which catalyze this reaction are known to the person skilled in the art in include, e.g., serine deaminases (EC 4.3.1.17; also referred to as L-serine ammonia-lyase) and threonine deaminases (EC 4.3.1.19; also known as threonine-ammonia-lyase).

An alternative route for converting serine into pyruvate goes from serine to hydroxypyruvate via an aminotransferase enzyme (2.6.1.X) or an amino acid dehydrogenase enzyme (EC 1.4.1.X). Hydroxypyruvate is then converted into glycerate by a hydroxypyruvate reductase (1.1.1.29 or 1.1.1.81), which is then further converted into 2-phosphoglycerate by a glycerate 2-kinase (2.7.1.165). The latter can be replaced by a combination of glycerate 3-kinase (EC 2.7.1.31) and phosphoglycerate mutase (EC 5.4.2.1). Phosphoglycerate can then be converted into phosphonopyruvate by an enolase (EC 4.2.1.11), which can then be converted into pyruvate by pyruvate kinase (EC 2.7.1.40).

The formaldehyde which is used in the condensation steps (1) and (5) of the method according to the invention can be provided by means and methods known to the person skilled in the art. In one embodiment, the formaldehyde is externally provided, i.e. added to the reaction mixture or to the culture medium in which an organism which is suitable for catalyzing the reactions of the method according to the invention is cultured.

In another embodiment, the formaldehyde is itself provided by an enzymatic conversion. The skilled person is aware of various substrates from which formaldehyde can be produced enzymatically. Examples are, e.g., methanol, formate, methane, halogenated methane and methylamine (or a derivative thereof) as well as methylated amino acids (e.g. sarcosine, betaine and glycine).

In a preferred embodiment the formaldehyde is provided by the enzymatic conversion of methanol into formaldehyde, preferably via an oxidation reaction.

One type of enzyme which can be used in this context is methanol dehydrogenase (NAD$^+$) which is classified as EC 1.1.1.244. This enzyme catalyzes the reaction:

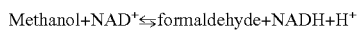

One example for such a methanol dehydrogenase which can be employed in a method according to the present invention is the methanol dehydrogenase encoded by the adhA gene of $C.\ glutamicum$. For this enzyme it has already been shown in the literature that it can convert methanol into formaldehyde (He et al., ACS Synthetic Biology 7 (2018), 1601-1611).

Another type of enzyme which can be used for the production of formaldehyde from methanol is methanol dehydrogenase (cytochrome c; also referred to as "quinone-dependent") which is classified as EC 1.1.2.7.

Another type of enzyme which can be used for the production of formaldehyde from methanol is a methanol oxidase, for example, methanol oxidases classified in EC 1.1.3.13

As mentioned above, the formaldehyde used in the condensation steps (1) and (5) of the method of the invention can also be provided by enzymatically producing it from methane. This can, e.g., be achieved by converting methane into methanol which, in turn, can then be converted into formaldehyde as described above. The conversion of methane into methanol can, e.g., be achieved by making use of a methane monooxygenase (EC 1.14.14.3 or 1.14.13.25).

As further mentioned above, the formaldehyde used in the condensation steps (1) and (5) of the method of the invention can also be provided by enzymatically producing it from halogenated methane. This can, e.g., be achieved by converting halogenated methane, e.g. dichloromethane, into formaldehyde. This conversion can, e.g., be achieved by making use of a dehalogenase, preferably a dehalogenase (classified in EC 4.5.1.3).

Another substrate from which formaldehyde may be produced enzymatically is methylamine (or a derivative thereof). Methylamine (or a derivative thereof) can, e.g., be converted into formaldehyde by oxidation. This can be achieved by making, e.g., use of a methylamine dehydrogenase (classified in EC 1.4.9.1) or of a primary amine oxidase (classified in EC 1.4.3.21).

Furthermore, formaldehyde can also be enzymatically provided starting from formate. It has, for example, been described in Siegel et al. (Proc. Natl. Acad. Sci. USA 24 (2015), 3704-3709) that formate can be converted by acetyl-CoA synthase (ACS) into formyl-CoA which can then be further converted into formaldehyde by making use of an acetaldehyde dehydrogenase (ACDH).

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method ae used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection. The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing enzymes described above for the conversions of the method according to the present invention as described herein above.

A method which employs a microorganism for carrying out a method according to the invention is referred to as an "in vivo" method. It is possible to use a microorganism which naturally produces the enzymes described above for the conversions of the method according to the present invention or a microorganism which had been genetically modified so that it expresses (including overexpresses) one or more of such enzymes.

In one embodiment, the microorganism used in a method of the invention is a microorganism which naturally expresses enzymes which catalyze steps (2), (3), (4) and (6) of the method of the invention and in which enzymes catalyzing steps (1) and (5) are overexpressed.

Thus, the microorganism can be an engineered microorganism which expresses at least some of the enzymes described above for the conversions of the method according to the present invention, i.e. which has in its genome (or on a plasmid) a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express all enzymes described above for the conversions of the method according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme(s) or the introduction of an efficient ribosomal binding site in order to increase the respective activity in said microorganism.

However, the invention preferably excludes naturally occurring microorganisms as found in nature expressing the enzymes as described above at levels as they exist in nature. Instead, the microorganism of the present invention and employed in a method of the present invention is preferably a non-naturally occurring microorganism, whether it has been genetically modified to express (including overexpression) at least one exogenous nucleic acid molecule not normally existing in its genome.

In one embodiment the (micro)organisms employed in connection with the present invention are preferably non-naturally occurring (micro)organisms, i.e. they are (micro) organisms which differ significantly from naturally occurring or (micro)organism and which do not occur in nature.

As regards the enzymes, they can be naturally occurring enzymes or they can be variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature. Such overexpression can lead to the direction of the metabolic flux in a correspondingly genetically modified microorganism into a certain direction. Such an overexpression can also force the reaction(s) of the method of the present invention which uses a non-natural substrate for the respective enzyme into a certain direction. Preferably, the term "overexpressed" means that the activity of the corresponding enzyme is at least 5%, 10%, 20%, 30% or 40% higher in a genetically modified microorganism expressing said enzyme than in a corresponding non-genetically modified microorganism.

Some of the steps of the method of the present invention (e.g. steps (1), (2) and (5)) rely on conversions which are understood not to be catalyzed by the respective enzymes according to their "natural" reaction. This means that the enzyme is known to naturally catalyze a different reaction, in particular uses a different substrate. The present invention makes use of the fact that it was found that certain enzymes are also able to use "non-natural" substrates and catalyze the respective conversion. The ability of an enzyme to use a "nor-natural" substrate is also referred to as a "promiscuous" activity. A "non-natural" substrate is understood to be a molecule that is not acted upon by the respective enzyme in nature (or only to a minor degree), even though it may actually coexist in the microorganism along with the endogenous enzyme. This "non-natural" substrate is not converted by the microorganism in nature (or only to a minor degree) as other substrates are preferred (e.g. the "natural substrate"). Thus, the present invention contemplates utilizing for certain steps enzymes which can accept a non-natural substrate.

It is also possible in the context of the present invention that the microorganism is a microorganism which naturally does not have one or more of the enzyme activities required by the method of the invention but which is genetically modified so as to comprise (a) nucleotide sequence(s) allowing the expression of (a) corresponding enzyme(s). Similarly, the microorganism may also be a microorganism which naturally has the respective enzyme activity/activities but which is genetically modified so as to enhance such (an) activity/activities, e.g. by the introduction of (an) exogenous nucleotide sequences encoding (a) corresponding enzyme(s) or by the introduction of a promoter for the endogenous gene(s) encoding the enzyme(s) to increase endogenous production to overexpressed (non-natural) levels.

If a microorganism is used which naturally expresses (a) corresponding enzyme(s), it is possible to modify such a microorganism so that the respective activity/activities is (are) overexpressed in the microorganism. This can, e.g., be achieved by effecting mutations in the promoter region of the corresponding gene(s) or introduction of a high expressing promoter so as to lead to a promoter which ensures a higher expression of the gene(s). Alternatively, it is also possible to mutate the gene(s) as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention.

In one embodiment the microorganism has been genetically modified to contain a foreign nucleic acid molecule encoding an enzyme which can catalyze the conversion of step (1) of the method according to the present invention.

In one embodiment the microorganism has been genetically modified to contain a foreign nucleic acid molecule encoding an enzyme which can catalyze the conversion of step (1) of the method according to the present invention and has been genetically modified to contain a foreign nucleic acid molecule encoding an enzyme which can catalyze the conversion of step (5) of the method according to the present invention.

The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma messi, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

In another embodiment the method according to the invention makes use of a microorganism which is able to metabolize methanol, e.g. a methanotrophic bacterium, a methylotrophic bacterium, a methanotrophic yeast or a methylotrophic yeast.

In another embodiment, the microorganism is a C1-fixing microorganism, preferably a recombinant C1-fixing microorganism. The nature of the C1-fixing microorganism is not particularly limited as long as it is a microorganism which is capable using carbon monoxide (CO) and gaseous substrates comprising CO like, e.g., syngas, as the source of carbon and energy. Syngas or synthesis gas is a mixture of CO and $CO_2$ as well as $H_2$. Corresponding naturally occurring (or genetically modified) microorganisms are known in the art that are capable of utilizing CO and converting it into acetyl-CoA. These organisms are often referred to as acetogenic microorganisms (sometimes also termed carboxydotrophic, acetogenic microorganisms). These microorganisms use the Wood-Ljungdahl pathway to fix CO and convert it into acetyl-CoA Examples of such microorganisms belong to the family Clostridiae and are, e.g., described in WO 2009/094485; WO 2012/05905; WO 2013/180584; US 201110238941; PNAS 107(29):13087-13092 (2010); Current Opinion in Biotechnology 23:364-381 (2012); Applied and Environmental Microbiology 77(15):5467-5475 (2011).

In certain embodiments, the C1-fixing microorganism is selected from the group of carboxydotrophic acetogenic bacteria. In preferred embodiments, the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bachii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kiuvi*.

In order to improve flux through the "homoserine cycle" when implemented in a microorganism, it may be advantageous to inactivate certain enzymatic activities which may endogenously occur in the respective microorganism.

Thus, in one embodiment, the microorganism in which the method of the invention is implemented is a microorganism which endogenously contains an operon encoding a formaldehyde detoxification system and in which this operon is deleted or rendered inactive. In a preferred embodiment, the microorganism belongs to the species *E. coli* and is a microorganism in which the formaldehyde detoxification (frmRAB) operon (Chen et al., Metabol. Engineering 49 (2018), 257-288) is deleted or rendered inactive. This system is also referred to as the glutathione-dependent formaldehyde oxidation system. The inactivation or deletion of this operon ensures that formaldehyde is not removed and is available for cell growth. In particular, the inactivation of this operon should avoid formaldehyde oxidation to formate which may lead to a depletion of the intracellular pool of formaldehyde.

In another embodiment, the microorganism in which the method of the invention is implemented is a microorganism which endogenously contains a gene(s) encoding (an) enzyme activity/activities which catalyze(s) the conversion of pyruvate into aspartate semialdehyde and in which this/these gene(s) is/are deleted or rendered inactive. In a preferred embodiment said gene is a gene encoding aspartate semialdehyde dehydrogenase (EC 1.2.1.11). In a preferred embodiment, the microorganism belongs to the species *E. coli* and is a microorganism in which the aid gene encoding said enzyme is deleted or rendered inactive.

In another embodiment, the microorganism in which the method of the invention is implemented is a microorganism which endogenously contains a gene encoding a 3-phosphoglycerate dehydrogenase (EC 1.1.1.95) and in which this gene is deleted or rendered inactive. In a preferred embodiment, the microorganism belongs to the species *E. coli* and is a microorganism in which the serA gene encoding said enzyme is deleted or rendered inactive.

In another embodiment, the microorganism in which the method of the invention is implemented is a microorganism which endogenously contains a gene encoding a serine hydroxymethyltransferase (EC 2.1.2.1) and in which this gene is deleted or rendered inactive. In a preferred embodiment, the microorganism belongs to the species *E. coli* and is a microorganism in which the glyA gene encoding said enzyme is deleted or rendered inactive.

In another embodiment, the microorganism in which the method of the invention is implemented is a microorganism which endogenously contains an operon encoding a glycin cleavage system (GCS) and in which this operon is deleted or rendered inactive. In a preferred embodiment, the microorganism belongs to the species *E. coli* and is a microorganism in which the glycine cleavage system (gcvTHP) operon is deleted or rendered inactive. The GCS operon in *E. coli* encodes for three enzymes, i.e. GcvT, GcvH and GcvP, and it is either possible to inactive the whole operon or one or more of the three genes.

In another embodiment, the microorganism in which the method of the invention is implemented is a microorganism which endogenously contains a gene encoding a bifunctional aspartokinase/homoserine dehydrogenase (EC 1.1.1.3) and in which this gene is deleted or rendered inactive. In a preferred embodiment, the microorganism belongs to the species *E. coli* and is a microorganism in which the thrA gene encoding said enzyme is deleted or rendered inactive.

In another embodiment, the microorganism in which the method of the invention is implemented is a microorganism which endogenously contains a gene encoding an L-threonine 3-dehydrogenase dehydrogenase (EC 1.1.1.103) and in which this gene is deleted or rendered inactive. In a preferred embodiment, the microorganism belongs to the species *E. coli* and is a microorganism in which the tdh gene encoding said enzyme is deleted or rendered inactive.

In another embodiment, the microorganism in which the method of the invention is implemented is a microorganism which endogenously contains agene encoding a 2-amino-3-ketobutyrate CoA ligase (EC 2.3.1.29) and in which this gene is deleted or rendered inactive. In a preferred embodiment, the microorganism belongs to the species *E. coli* and is a microorganism in which the kbl gene encoding said enzyme is deleted or rendered inactive.

In another embodiment, the microorganism in which the method of the invention is implemented is a microorganism which endogenously contains a gene encoding a lactate dehydrogenase (EC 1.1.1.28) and in which this gene is deleted or rendered inactive. In a preferred embodiment, the microorganism belongs to the species *E. coli* and is a microorganism in which the AMA gene encoding said enzyme is deleted or rendered inactive.

In another embodiment the microorganism shows any possible combination of gene deletions as described above.

It is also conceivable to use in the method according to the invention a combination of microorganisms wherein different microorganisms express different enzymes as described above. The genetic modification of microorganisms to express an enzyme of interest will also be further described in detail below.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harbouring the above described enzyme(s). Ina bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, fed-batch-culture, perfusion culture or chemostate-culture, all of which are generally known in the art.

The culture medium can be any culture medium suitable for cultivating the respective organism or microorganism.

When carried out by making use of a microorganism, the method according to the present invention may, e.g. be designed as a continuous fermentation culturing method or as a batch culture or any suitable culture method known to the person skilled in the art.

The enzymes used in the method according to the invention can be a naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, NY, USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention may be a microorganism which has been genetically modified by the introduction of a nucleic acid molecule encoding a corresponding enzyme. Preferably, the microorganism is a microorganism according to the present invention as described herein below. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. Preferably, the nucleic acid molecule introduced into the microorganism is a nucleic acid molecule which is heterologous with respect to the microorganism, i.e. it does not naturally occur in said microorganism.

In the context of the present invention, an "increased activity" preferably means that the expression and/or activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably inked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, NY, USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, NY, USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-518, in Bitter et al. (Methods in Enzymology 153 (1987), 516-544) and in Sewers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 485496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier at al., Methods in Enzymology 185 (1990), 60-89), lacUV5, trp, trp-lacUV5 (DeBoer at al., in Rodriguez and Chamberlin (Eds), Promoters, Structure and Function; Praeger, New York, (1962), 462-481; DeBoer et al., Proc. Natl. Acad. Sci. USA (1983), 21-25), Ip1, rac (Boros et al., Gene 42 (1988), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-G-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, NY, USA; Methods in Yeast Genetics, A Laboratory Course Manuel, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention furthermore relates to a recombinant microorganism expressing enzymes for catalyzing the following reactions:
(1) condensation of pyruvate with formaldehyde into 4-hydroxy-2-oxobutanoic acid (HOB) by an aldolase classified in EC 4.1.2._;
(2) amination of the thus produced 4-hydroxy-2-oxobutanoic acid (HOB) to produce homoserine by an aminotransferase enzyme classified in EC 2.6.1._ or by an amino acid dehydrogenase (EC 1.4.1._);
(3) phosphorylation of thus produced homoserine to produce o-phosphohomoserine by a homoserine kinase (EC 2.7.1.39);
(4) dephosphorylation of the thus produced o-phosphohomoserine to produce threonine by a threonine synthase (EC 4.2.3.1);
(5) conversion of the thus produced threonine into glycine by a threonine aldolase (selected from the group consisting of EC 4.1.2.5, EC 4.1.2.6, EC 4.1.2.48 and EC 4.1.2.49) or by a combination of a threonine dehydrogenase (EC 1.1.1.103) and a 2-amino-3-ketobutyrate CoA ligase (EC 2.3.1.29);
(6) condensation of the thus produced glycine with formaldehyde to produce serine by a threonine aldolase (selected from the group consisting of EC 4.1.2.5. EC 4.1.2.6. EC 4.1.2.48 and EC 4.1.2.49); and
(7) deamination of the thus produced serine to produce pyruvate by a serine deaminase (EC 4.3.1.17) or a threonine deaminase (EC 4.3.1.19), wherein said pyruvate can then be used as a substrate in step (1), wherein said microorganism contains at least one heterologous nucleic acid molecule encoding the aldolase catalyzing step (1) and
overexpresses the enzyme catalyzing step (6), i.e. the condensation of glycine with formaldehyde to form serine.

In a preferred embodiment, the microorganism further overexpresses at least one of the enzymes catalyzing step (3), step (4) or step (5).

As regards the enzymes mentioned in items (1) to (7) above and preferred embodiments thereof and as regards the preferred embodiments of the microorganism, the same applies as has been described above in connection with the method according to the invention.

The microorganism of the present invention may be a microorganism which is recombinant for all of the enzymatic activities listed in items (1) to (7) above, wherein the term "recombinant" means that the microorganism is transformed with heterologous nucleic acid molecules encoding the respective enzymes. These heterologous nucleic acid molecules may be integrated into the genome of the microorganisms or may be present as extrachromosomal elements. Chromosomal location is preferred. Thus, in such a case the "homoserine cycle" is established in the respective microorganism by introducing for all the required enzymatic activities the corresponding nucleic acid molecules encoding them. The enzymes encoded by the nucleic acid molecules may be enzymes which endogenously occur in the microorganism but are overexpressed due to the use of heterologous regulatory regions such as heterologous promoter and/or ribosomal binding sites. Alternatively, the enzymes may be enzymes which do not naturally occur in the respective microorganism.

However, the "homoserine cycle" described in the present application shows the advantage that it relies in part on enzymatic activities which are expressed endogenously in a large variety of microorganisms and in particular to such a level that they are able to support the metabolic flux through the cycle. Accordingly, the microorganism according to the present invention may also be a microorganism in which one or more of the enzymatic activities of items (1) to (7), above, occur endogenously. However, in such a case the enzyme activity of ten (1) is recombinantly introduced into such an organism and, if it already endogenously occurs in such a microorganism, it is overexpressed. Moreover, it is preferred that one or more of endogenously occurring enzymatic activities listed in items (2) to (7) are overexpressed in the corresponding microorganism. The term "overexpression" means that the enzymatic activity of the respective enzyme is increased in the microorganism in comparison to the parent strain and in particular in comparison to the expression level of the endogenously occurring gene, preferably by at least 5%, 10%, 20%, 30% or by at least 40%. Such an increase may be due to an increase of expression of the corresponding gene. Such an increase of expression can, e.g., be achieved by placing the coding sequence of the respective gene under the control of a heterologous promoter, in particular a heterologous promoter which ensures a higher expression of the gene. Alternatively, the endogenous promoter of the gene can be mutated so as to lead to a higher expression of the gene. Such a promoter replacement or mutation can be effected in the endogenous gene located on the chromosome of the microorganism or the corresponding modified gene with a stronger promoter can be placed on a plasmid. An example for a strong promoter which can be used to slow for the overexpression of the aldolase gene is the constitutive strong promoter pgi-20 (Braatsch et al., Biotechniques 45 (2008), 335-337).

In addition, in order to allow for an increased expression, it can also be advantageous to use an efficient ribosome binding site. In this respect, the term "heterologous" also includes the situation in which the respective gene is modified so as to comprise a ribosome binding site which is different from its natural ribosomal binding site and which allows for an increased expression (translation) of the gene. An example of a suitable binding site is the ribosome binding site "C" (AAGTTAAGAGGCAAGA (SEQ ID NO: 44)) (Zelcbuch et al., Nucleic Acids Res. 41 (2013), e98).

Another possibility for obtaining an increased enzymatic activity is the expression of a mutated enzyme which shows an increased activity for the respective reaction in comparison to the non-mutated enzyme.

The term "increase of expression" also covers the possibility that the activity of the enzyme is increased due to a mutation in the protein which leads to a higher activity. Means and methods for improving enzyme activity by way of mutation have been described above.

In one preferred embodiment, the microorganism is a microorganism which endogenously expresses a homoserine kinase (EC 2.7.1.39) and in which the homoserine kinase (EC 2.7.1.39) is overexpressed in comparison to the parent strain.

In another preferred embodiment, the microorganism is a microorganism which endogenously expresses a threonine synthase (EC 4.23.1) and in which the threonine synthase (EC 4.2.3.1) is overexpressed in comparison to the parent strain.

In a further preferred embodiment, the microorganism is a microorganism which endogenously expresses a threonine aldolase (selected from the group consisting of EC 4.1.2.5, EC 4.1.2.6, EC 4.1.2.48 and EC 4.1.2.49) and in which a threonine aldolase (selected from the group consisting of EC 4.1.2.5, EC 4.1.2.6, EC 4.1.2.48 and EC 4.1.2.49) is overexpressed in comparison to the parent strain.

In another preferred embodiment, the microorganism is a microorganism which endogenously expresses a threonine dehydrogenase (EC 1.1.1.103) and a 2-amino-3-ketobutyrate CoA ligase (EC 2.3.1.29) and in which the threonine dehydrogenase (EC 1.1.1.103) and the 2-amino-3-ketobutyrate CoA ligase (EC 2.3.1.29) is overexpressed in comparison to the parent strain.

In another preferred embodiment, the microorganism is a microorganism which endogenously expresses an aminotransferase enzyme classified in EC 2.6.1._ or an amino acid dehydrogenase (EC 1.4.1._) which can convert 4-hydroxy-2-oxobutanoic acid (HOB) into homoserine and in which said aminotransferase enzyme classified in EC 2.6.1._ or said amino acid dehydrogenase (EC 1.4.1._) is overexpressed in comparison to the parent strain.

In another preferred embodiment, the microorganism is a microorganism which endogenously expresses a serine deaminase (EC 4.3.1.17) or a threonine deaminase (EC 4.3.1.19) and in which the serine deaminase (EC 4.3.1.17) or the threonine deaminase (EC 4.3.1.19) is overexpressed in comparison to the parent strain.

In another embodiment, the microorganism overexpresses any possible combination of enzymes mentioned above for catalyzing steps (2) to (7). In a preferred embodiment, the microorganism overexpresses enzymes catalyzing steps (3) and (4), or overexpresses enzymes catalyzing steps (3) and (5), or overexpresses enzymes catalyzing steps (3) and (5), or overexpresses enzymes catalyzing steps (3), (4) and (5).

The microorganism may be a microorganism which endogenously expresses all the enzyme activities as specified in item (1) to (7) above but which is recombinant for at least the enzyme activity specified in item (1), i.e. an aldolase classified in EC 4.1.2._. The term "recombinant" in this context means that the microorganism contains a heterologous nucleic acid molecule encoding the corresponding aldolase. In this context, the aldolase itself may be endogenous to the microorganism but the term "heterologous" in this case means that the aldolase is encoded by a nucleic acid where the coding region is not in its natural context. Preferably, the coding region is either not located at the genomic location where it is naturally located (i.e. It is located at a different position in the genome or it is located on an extrachromosomal element such as a plasmid) and/or, it is linked to heterologous regulatory regions, such as a promoter. It is preferred that the gene encoding the aldolase is modified in such a manner that its expression is increased in comparison to the expression of the corresponding endogenous gene, preferably by at least 5%, 10%, 20%, 30% or by at least 40%. Such an increase of expression (herein also referred to as "overexpression") can, e.g., be achieved by placing the coding sequence of the aldolase under the control of a heterologous promoter, in particular a heterologous promoter which ensures a higher expression of the gene. Alternatively, the endogenous promoter of the gone can be mutated so as to lead to a higher expression of the gene. Such a promoter replacement or mutation can be effected in the endogenous gene located on the chromosome of the microorganism or the corresponding modified gone with a stronger promoter can be placed on a plasmid. An example for a strong promoter which can be used to allow for the overexpression of the aldolase gene is the constitutive strong promoter pgi-20 (Braatsch et al., Biotechniques 45 (2008), 335-337).

In addition, in order to allow for an increased expression, it can also be advantageous to use an efficient ribosome binding site. In this respect, the term "heterologous" also includes the situation in which the aldolase gene is modified so as to comprise a ribosome binding site which is different from its natural ribosomal binding site and which allows for an increased expression (translation) of the gene. An example of a suitable binding site is the ribosome binding site "C" (AAGTTAAGAGGCAAGA (SEQ ID NO: 44)) (Zelcbuch et al., Nucleic Acids Res. 41 (2013), e98).

The term increase of expression also covers the possibility that the activity of the enzyme is increased due to a mutation in the protein which leads to a higher activity. Means and methods for improving enzyme activity by way of mutation have been described above.

The microorganism of the present invention may be a bacterium, a fungus, such as a yeast, an alga or an archae. In one preferred embodiment, the microorganism is a bacterium. Preferred bacteria are bacteria of the genus *Bacillus*, *Clostridium*, *Corynebacterium*, *Pseudomonas*, *Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas moblils* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces*, *Schizosaccharomyces*, *Aspergillus*, *Trichoderma*, *Kluyveromyces* or *Pichia* and even more preferably of the species *Saccharomyces cerevisae*, *Schizosaccharomyces pombe*, *Aspergillus niger*, *Trichoderma reesei*, *Kluyveromyces marxianus*, *Kluyveromyces lactis*, *Pichia pastoris*, *Pichia torula* or *Pichia utilis*.

In another embodiment, the microorganism is a photosynthetic microorganism, preferably a photosynthetic bacterium, or a microalga. In a further embodiment the microorganism is an alga, more preferably an alga belonging to the diatomeae.

In another embodiment the microorganism is a microorganism which is able to metabolize methanol. In one embodiment, the microorganism is naturally able to metabolize methanol and is, e.g. a methanotrophic bacterium, a methylotrophic bacterium, a methanotrophic yeast or a methylotrophic yeast.

In another embodiment, the microorganism is a C1-fixing microorganism, preferably a recombinant C1-fixing microorganism. The nature of the C1-fixing microorganism is not particularly limited as long as it is a microorganism which is capable using carbon monoxide (CO) and gaseous substrates comprising CO like, e.g., syngas, as the source of carbon and energy. Syngas or synthesis gas is a mixture of CO and $CO_2$ as well as $H_2$. Corresponding naturally occurring (or genetically modified) microorganisms are known in the art that are capable of utilizing CO and converting it into acetyl-CoA. These organisms are often referred to as acetogenic microorganisms (sometimes also termed carboxydotrophic, acetogenic microorganisms). These microorganisms use the Wood-Ljungdahl pathway to fix CO and convert it into acetyl-CoA. Examples of such microorganisms belong to the family Clostridiae and are, e.g., described in WO 2009/0494485; WO 2012/05905; WO 2013/180584; US 2011/0238941; PNAS 107(29):13087-13092 (2010); Current Opinion in Biotechnology 23:364-381 (2012); Applied and Environmental Microbiology 77(15):5467-5475 (2011).

In certain embodiments, the C1-fixing microorganism is selected rom the group of carboxydotrophic acetogenic bacteria. In preferred embodiments, the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicus, Acetobacterium woodii, Alkalibaculum brachii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one embodiment, the microorganism is capable of converting methanol into formaldehyde. In a preferred embodiment microorganism is capable of providing formaldehyde by the enzymatic conversion of methanol into formaldehyde, preferably via an oxidation reaction.

One type of enzyme which can be used in this context is methanol dehydrogenase (NAD*) which is classified as EC 1.1.1.244. This enzyme catalyzes the reaction:

Methanol+NAD$^+$⇌formaldehyde+NADH+H$^+$

Thus, the microorganism is preferably expressing such an enzyme, either endogenously or because it has been genetically modified so as to contain a nucleic acid molecule which encodes such an enzyme. One example for such a methanol dehydrogenase is the methanol dehydrogenase encoded by the adhA gene of *C. glutamicum.*

Another type of enzyme which can be used for the production of formaldehyde from methanol is methanol dehydrogenase (cytochrome c; also referred to as "quinone-dependent") which is classified as EC 1.1.2.7. Thus, the microorganism is preferably expressing such an enzyme, either endogenously or because it has ben genetically modified so as to contain a nucleic acid molecule which encodes such an enzyme.

Another type of enzyme which can be used for the production of formaldehyde from methanol is a methanol oxidase, for example, methanol oxidases classified in EC 1.1.3.13. Thus, the microorganism is preferably expressing such an enzyme, either endogenously or because it has been genetically modified so as to contain a nucleic acid molecule which encodes such an enzyme.

In one embodiment, the microorganism is capable of converting methane into formaldehyde. Preferably, the microorganism is able to convert methane into methanol and to further convert methanol into formaldehyde. The conversion of methane into methanol can, e.g., be achieved by making use of a methane monooxygenase (EC 1.14.14.3 or 1.14.13.25). Thus, the microorganism is preferably expressing such (an) enzymes, either endogenously or because it has been genetically modified so as to contain (a) nucleic acid molecules which encode(s) such (an) enzyme(s).

In one embodiment, the microorganism is capable of converting halogenated methane into formaldehyde. Preferably, the microorganism is able to convert halogenated methane, e.g. dichloromethane, into formaldehyde. This conversion can, e.g., be achieved by making use of a dehalogenase, preferably a dehalogenase classified in EC 4.5.1.3). Thus, the microorganism is preferably expressing such an enzyme, either endogenously or because it has been genetically modified so as to contain a nucleic acid molecule which encodes such an enzyme.

In one embodiment, the microorganism is capable of converting methylamine (or a derivative thereof) into formaldehyde. Preferably, the microorganism is able to convert methylamine (or a derivative thereof) into formaldehyde by oxidation. This can be achieved by making, e.g., use of a methylamine dehydrogenase (classified in EC 1.4.9.1) or of a primary amine oxidase (classified in EC 1.4.3.21). Thus, the microorganism is preferably expressing such (an) enzymes, either endogenously or because it has been genetically modified so as to contain (a) nucleic acid molecules which encode(s) such (an) enzyme(s).

In one embodiment, the microorganism is capable of converting formate into formaldehyde. It has, for example, been described in Siegel et al. (Proc. Natl. Acad. Sci. USA 24 (2015), 3704-3709) that formate can be converted by acetyl-CoA synthase (ACS) into formyl-CoA which can then be further converted into formaldehyde by making use of an acetaldehyde dehydrogenase (ACDH). Thus, the microorganism is preferably expressing such an enzyme, either endogenously or because it has been genetically modified so as to contain a nucleic acid molecule which encodes such an enzyme.

In order to improve flux through the "homoserine cycle" when implemented in a microorganism, it may be advantageous to inactivate certain enzymatic activities which may endogenously occur in the respective microorganism.

Thus, in one embodiment, the microorganism is a microorganism which endogenously contains an operon encoding a formaldehyde detoxification system and in which this operon is deleted or rendered inactive. In a preferred embodiment, the microorganism belongs to the species *E. coli* and is a microorganism in which the formaldehyde detoxification (frmRAB) operon (Chen et al., Metabol. Engineering 49 (2018), 257-266) is deleted or rendered inactive. This system is also referred to as the glutathione-dependent formaldehyde oxidation system. The inactivation or deletion of this operon ensures that formaldehyde is not removed and is available for cell growth. In particular, the inactivation of this operon should avoid formaldehyde oxidation to formate which may lead to a depletion of the intracellular pool of formaldehyde.

In another embodiment, the microorganism is a microorganism which endogenously contains a gene(s) encoding (an) enzyme activity/activities which catalyze(s) the conversion of pyruvate into aspartate semialdehyde and in which this/these gene(s) is/are deleted or rendered inactive. In a preferred embodiment said gene is a gene encoding aspartate semialdehyde dehydrogenase (EC 1.2.1.11). In a preferred embodiment, the microorganism belongs to the species *E. coli* and is a microorganism in which the asd gene encoding said enzyme is deleted or rendered inactive.

In another embodiment, the microorganism is a microorganism which endogenously contains a gene encoding a 3-phosphoglycerate dehydrogenase (EC 1.1.1.95) and in which this gene is deleted or rendered inactive. In a preferred embodiment, the microorganism belongs to the species *E. coli* and is a microorganism in which the serA gene encoding said enzyme is deleted or rendered inactive.

In another embodiment, the microorganism is a microorganism which endogenously contains a gene encoding a serine hydroxymethyltransferase (EC 2.1.2.1) and in which this gene is deleted or rendered inactive. In a preferred embodiment, the microorganism belongs to the species *E. coli* and is a microorganism in which the glyA gene encoding said enzyme is deleted or rendered inactive.

In another embodiment, the microorganism is a microorganism which endogenously contains an operon encoding a glycin cleavage system (GCS) and in which this operon is deleted or rendered inactive. In a preferred embodiment, the microorganism belongs to the species *E. coli* and is a microorganism in which the glycine cleavage system (gv7HP) operon is deleted or rendered inactive. The GCS operon in *E. coli* encodes for three enzymes, i.e. GcvT, GcvH and GcvP, and it is either possible to inactive the whole operon or one or more of the three genes.

In another embodiment, the microorganism is a microorganism which endogenously contains a gene encoding a bifunctional aspartokinase/homoserine dehydrogenase (EC 1.1.1.3) and in which this gene is deleted or rendered inactive. In a preferred embodiment, the microorganism belongs to the species *E. coli* and is a microorganism in which the thrA gene encoding said enzyme is deleted or rendered inactive.

In another embodiment, the microorganism is a microorganism which endogenously contains a gene encoding an L-threonine 3-dehydrogenase dehydrogenase (EC 1.1.1.103) and in which this gene is deleted or rendered inactive. In a preferred embodiment, the microorganism belongs to the species *E. coli* and is a microorganism in which the tdh gene encoding said enzyme is deleted or rendered inactive.

In another embodiment, the microorganism is a microorganism which endogenously contains a gene encoding a 2-amino-3-ketobutyrate CoA ligase (EC 2.3.1.29) and in which this gene is deleted or rendered inactive. In a preferred embodiment, the microorganism belongs to the species *E. coli* and is a microorganism in which the kbl gene encoding said enzyme is deleted or rendered inactive.

In another embodiment, the microorganism is a microorganism which endogenously contains a gene encoding a lactate dehydrogenase (EC 1.1.1.28) and in which this gene is deleted or rendered inactive. In a preferred embodiment, the microorganism belongs to the species *E. coli* and is a microorganism in which the ldhA gene encoding said enzyme is deleted or rendered inactive.

In another embodiment the microorganism shows any possible combination of gene deletions/inactivations as described above.

FIG. 1 shows a schematic version of a representative example of the enzymatic steps involved in the method according to the present invention for incorporating formaldehyde.
(1) Condensation of pyruvate with formaldehyde into 4-hydroxy-2-oxobutanoic acid (HOB) via an aldolase; (2) amination of the thus produced 4-hydroxy-2-oxobutanoic acid (HOB) to produce homoserine; (3) phosphorylation of thus produced homoserine to produce o-phosphohomoserine; (4) dephosphorylation of the thus produced o-phosphohomoserine to produce threonine; (5) conversion of the thus produced threonine into glycine and acetaldehyde; (6) condensation of the thus produced glycine with formaldehyde to produce serine; and (7) conversion of the thus produced serine to produce pyruvate. Reactions based on promiscuous enzyme activities are shown in color.

Figure 2:
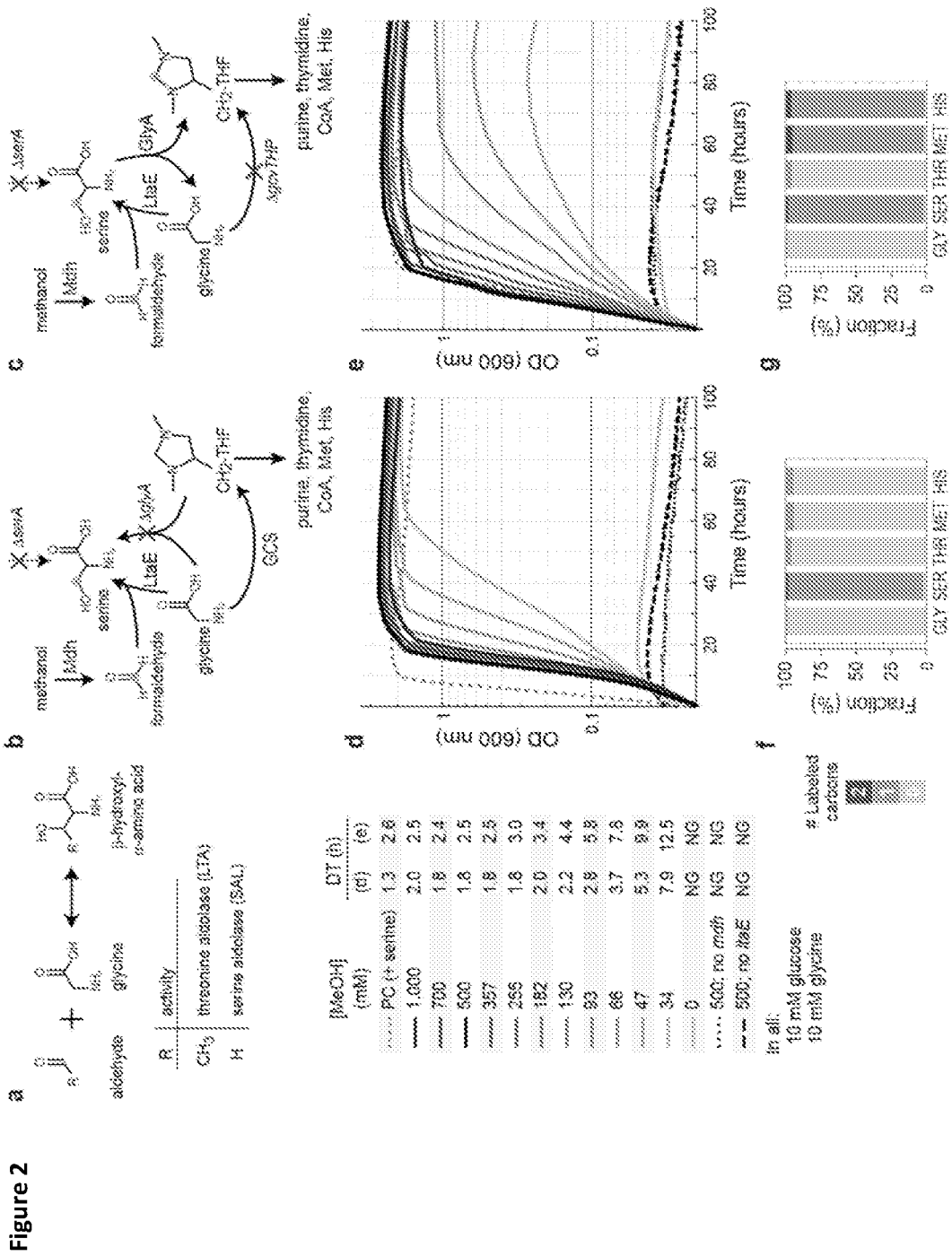

FIG. 2 shows in vivo 'serine aldolase' (SAL) activity catalyzed by LtaE: (a) LtaE catalyzes aldol condensation between glycine and different aldehyde. Threonine aldol (LTA) is its primary function, while seine aldolase is a promiscuous activity (Contestabile et al., Eur. J. Biochem. 268 (2001), 65084525). (b), (c) two selection schemes for the in vivo activity of the SAL reaction. Carbon sources are shown in purple (glucose not shown) while the formaldehyde moiety is shown is green. (b) ΔfrmRAB ΔserA ΔglyA strain in which methanol assimilation is required for the biosynthesis of swine. (c) ΔfrmRAB ΔserA ΔgcvTHP strain, in which methanol assimilation is required for the biosynthesis of serine and the cellular $C_1$ moieties. (d), (e) Growth with different concentrations of methanol confirm the activity of the SAL reaction. In all cases, 10 mM glucose and 10 mM glycine were added to the medium. Methanol dehydrogenase (mdi) and ltaE were expressed from a plasmid. Each growth curve represents the average of three replicates, which differ from each other by les than 5%. (f), (g) Labeling pattern of proteinogenic glycine (GLY), serine (SER), threonine (THR), methionine (MET) and histidine (HIS) upon feeding with $^{13}$C-methanol as well as unlabeled glucose and glycine.

Figure 3:
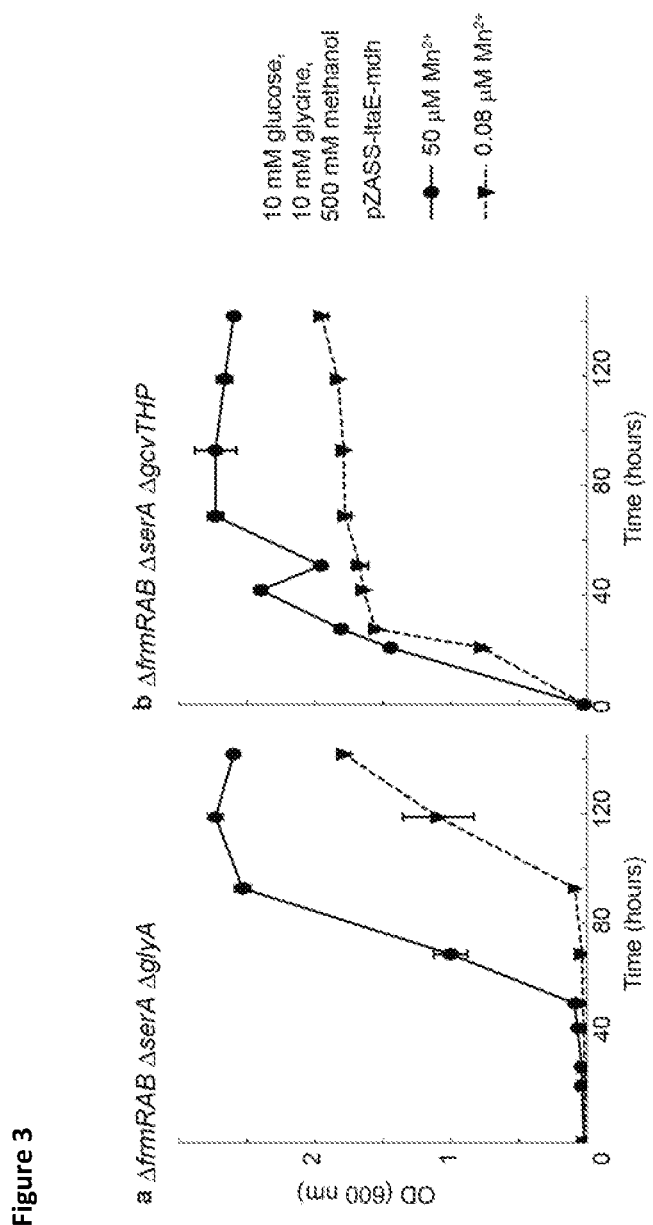

FIG. 3 shows that $Mn^{2+}$ supplementation improves LtaE dependent growth. While $Mn^{2+}$ is a cofactor of LtaE, M medium contains only 0.08 μM $Mn^{2+}$. Addition of 50 μM $MnCl_2$ increases the growth rate and yield of the LtaE-dependent strains. Error bars represent standard deviations, n=3.

Figure 4:
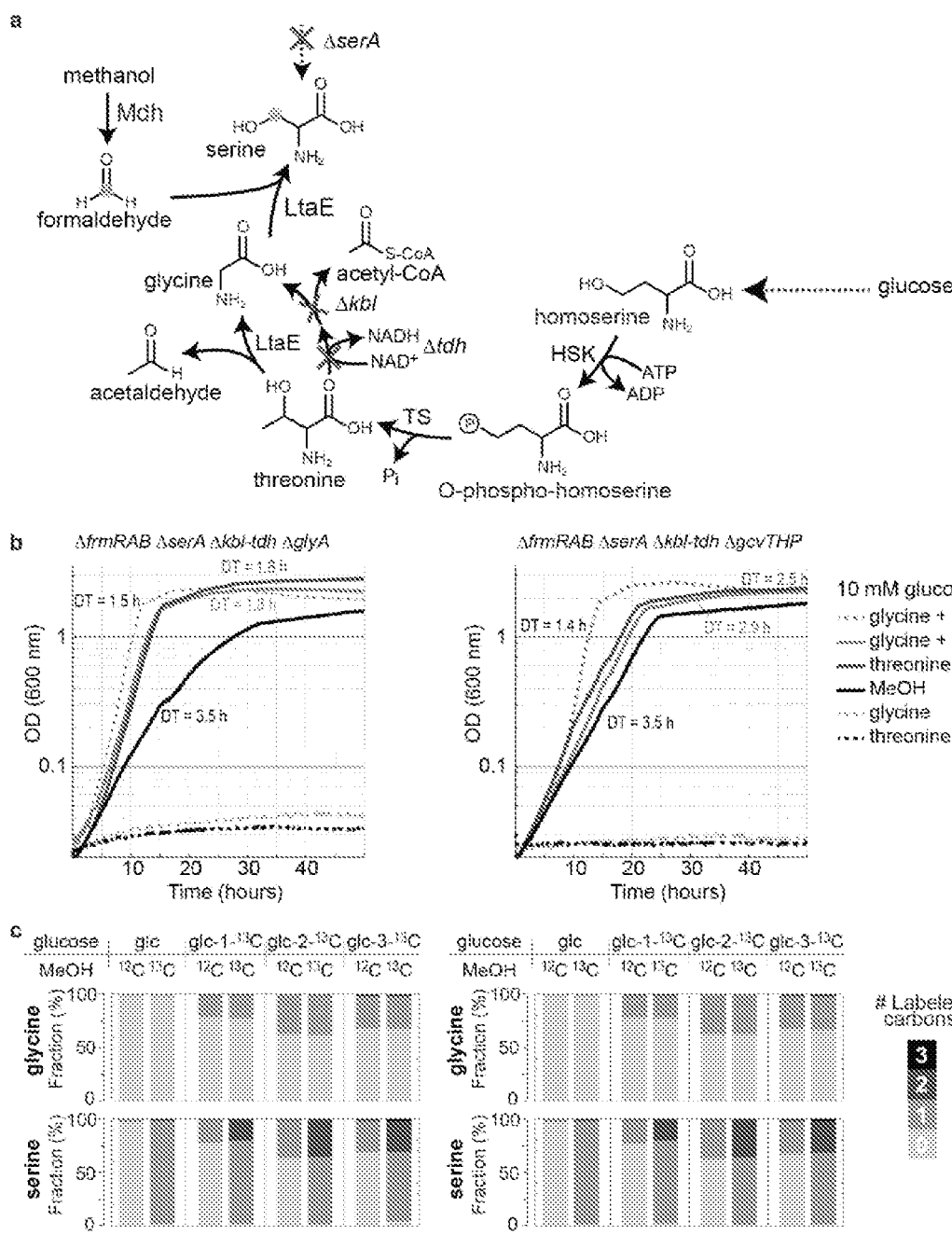

FIG. 4 Figure shows that LtaE can operate as threonine aldolase and serine aldolase simultaneously. (a) Selection scheme for serine and glycine production from threonine and homoserine. (b) The two selection strains, deleted in the LtaE-independent threonine cleavage system (Δkbl-tdh), can grow with methanol as serine precursor. Glycine is either provided externally (10 mM, black lines) or produced internally, either from externally added threonine (10 mM, red lines) or from the internal pool of threonine (green lines). The latter growth confirms that LtaE can catalyze the LTA and SAL reactions simultaneously. In all cases, 10 mM glucose and 500 mM methanol were added. Each growth curve represents the average of three replicates, which differ from each other by less than 5%. (c) Labeling pattern of proteinogenic glycine and serine upon feeding with glucose labeled at different carbon as well as labeled or unlabeled methanol. This labeling confirms that all cellular serine is produced from glycine and methanol even when glycine is produced internally from threonine biosynthesis and degradation.

FIG. 6 shows in vivo activity of enzymes condensing pyruvate and formaldehyde into HOB and converting HOB into homoserine, respectively. (a) A selection scheme for the in vivo activity of the reactions of condensing pyruvate and formaldehyde into HOB and converting HOB into homoserine. Carbon sources are shown in purple while the formaldehyde moiety is shown is green. (b) Several *E. coli* enzymes are known to catalyze an aldolase reaction with pyruvate as acceptor and might be able to accept formaldehyde as a donor. The sequence similarity of these enzyme is indicated by the schematic tree to the left. (c) Four tested aldolases, once overexpressed together with methanol dehydrogenase, support growth of the selection strain. Glucose was added at 10 mM, methanol at 500 mM, diaminopimelate at 0.25 mM, and isoleucine at 1 mM. Each growth curve represents the average of three replicates, which differ rom each other by less than 5%. (d) Labeling pattern of proteinogenic methionine (MET), threonine (THR), lysine (LYS), and aspartate (ASP) upon feeding with unlabeled glucose, diaminopimelate and isoleucine as well as $^{13}$C-methanol. The results confirm that all cellular threonine and methionine are derived from the enzymatic activity condensing pyruvate with formaldehyde and from the aminase reaction.

FIG. 6 shows a multiple sequence alignment of candidate enzymes condensing pyruvate and formaldehyde into HOB. Protein sequence of RhmA/YfaU (P76469; SEQ ID NO:1), GarL (P23522; SEQ ID NO:4), YagE (P75682; SEQ ID NO:2), YjhH (P39359; SEQ ID NO:3), Eda (P0A955; SEQ ID NO: 45), DgoA (Q68F16; SEQ ID NO: 46) and MhpE (P51020; SEQ ID NO: 47) were obtained from UniProt. Sequence alignment was produced by MAFFT (Katoh and Standley, Mol. Biol. Evol. 30 (2013), 772-780. ESPpript 3.0 (Rober and Gouet, 42 (2014), W320-W324) was used for displaying the aligned sequences with the 3D structure of GarL, 1dxe (Izard and Blackwell, EMBO J. 19 (2000), 3849-3856). Protein α-helixes and β-sheets are indicated above, sequence consensus >70% are show in cons.

FIG. 7 shows protein structure based alignments of candidate enzymes condensing pyruvate and formaldehyde into HOB. Available protein structures, 1dxf (Izard and Blackwell, EMBO J. 19 (2000), 3849-3856) for GarL, 2vwt (Res et al., Biochemistry-US 47 (2006), 9955-9965) for RhmA, 4ptn (Manicka et al., Proteins 71 (2008), 2102-2108) for YagE, 2v82 (Walters et al., Bioorganic & Medicinal Chemistry 16 (2008), 710-720) for DgoA and 1eua (Allard et al., Proc. Natl Acad. Sci. USA 98 (2001), 3679-3684) for Eda were obtained from RCSB PDB. Structures was aligned by TM-align (Zhang et al., Nucleic Acids Res. 33, 2302-2309 (2005). within PyMOL. Results of the alignments, RMSD and TM-score, are shown in the table. The figures were rendered using PyMOL.

Figure 8:
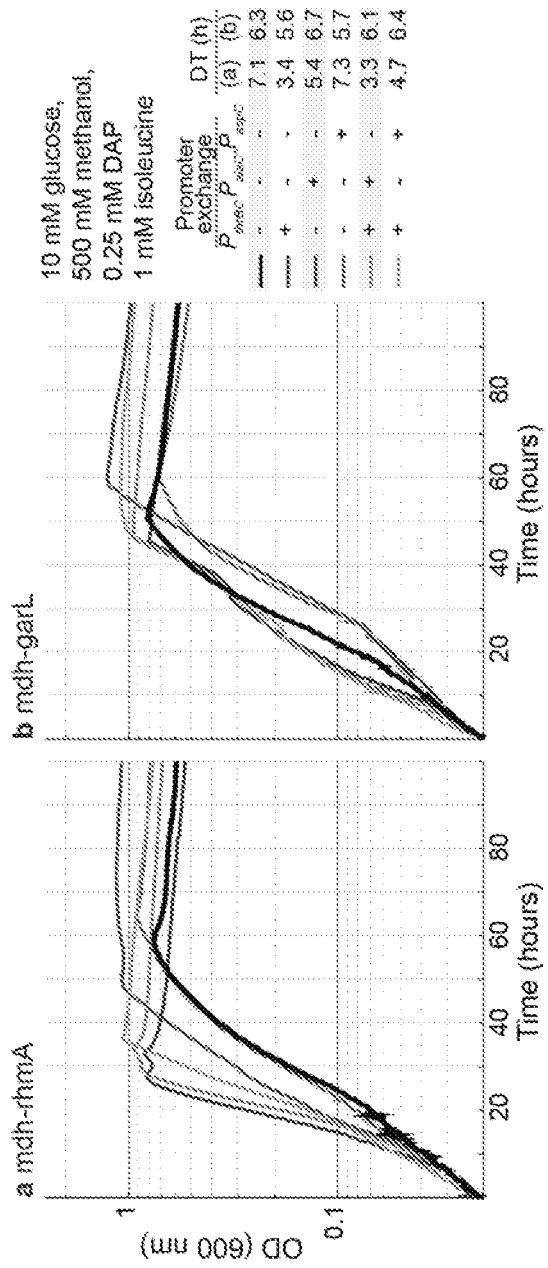

FIG. 8 shows effects of genomic overexpression of the enzyme of the homoserine cycle. ThrB (HSK), ThrC (TS), AlaC* (AlaC A142P Y275D) or AspC were overexpressed by exchanging their native promoters with synthetic promoters within the selection strain ΔfrmRAB Δasd. Each growth curve represents the average of three replicates, which differ from each other by less than 5%.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

To confirm the in vivo feasibility of the homoserine cycle, several *E. coli* gene deletion strains were constructed whose growth is coupled to the activity of different pathway segments. Using this approach it could be demonstrated that all required promiscuous enzymes are active enough to enable growth of the auxotrophic strains.

Methods

Strains and genomic manipulation. Strains used in this study are listed in Table 1.

TABLE 1

LIST OF *E. COLI* STRAINS

| STRAIN | GENOTYPE | REFERENCE OR SOURCE |
| --- | --- | --- |
| MG1655 | K-12 F$^-$ λ$^-$ ILVG$^-$ RFB-50 RPH-1 | LAB COLLECTION |
| SIJ488 | MG1655 TN7::PARA-EXO-BETA-GAM; PRHA-F$^-$ ENDA1 GLNV44 THI-1 RECA1 RELA1 GYRA96 | 1 |
| DH5A | DEOR NUPG PURB20 φ80DLACZΔM15 Δ(LACZYA-ARGF)U169, HSDR17($R_K^-$ $M_K^+$), λ$^-$ | LAB COLLECTION |
|  | SIJ488 ΔFRMRAB ΔSERA ΔGLYA | THIS STUDY |
|  | SIJ488 ΔFRMRAB ΔSERA ΔGCVTHP | THIS STUDY |
|  | SIJ488 ΔFRMRAB ΔSERA ΔGLYA ΔKBL-TDH | THIS STUDY |
|  | SIJ488 ΔFRMRAB ΔSERA ΔGCVTHP ΔKBL-TDH | THIS STUDY |
|  | SIJ488 ΔFRMRAB ΔASD | THIS STUDY |
| PTHRBC_D | SIJ488 ΔP$_{THRLABC}$::CAP-P$_{PGI-20}$-THRBC | THIS STUDY |
| PALAC_D | SIJ488 ΔP$_{ALAC}$::CAP-P$_{PGI-20}$-ALAC* | THIS STUDY |
| PASPC_D | SIJ488 ΔP$_{ASPC}$::CAP-P$_{PGI-20}$-ASPC | THIS STUDY |
|  | SIJ488 ΔFRMRAB ΔASD ΔP$_{THRLABC}$::P$_{PGI-20}$-THRBC | THIS STUDY |
|  | SIJ488 ΔFRMRAB ΔASD ΔP$_{ALAC}$::P$_{PGI-20}$-ALAC* | THIS STUDY |
|  | SIJ488 ΔFRMRAB ΔASD ΔP$_{ASPC}$::P$_{PGI-20}$-ASPC | THIS STUDY |
|  | SIJ488 ΔFRMRAB ΔASD ΔP$_{THRLABC}$::P$_{PGI-20}$-THRBC ΔP$_{ALAC}$::P$_{PGI-20}$-ALAC* | THIS STUDY |
|  | SIJ488 ΔFRMRAB ΔASD ΔP$_{THRLABC}$::P$_{PGI-20}$-THRBC ΔP$_{ASPC}$::P$_{PGI-20}$-ASPC | THIS STUDY |

[1] Jensen et al. (Sci. Rep. 5 (2015), 17874)

An *E. coli* MG1655 derived strain SIJ488 (Jensen et al., Scientific Reports 5 (2015), 17874) was used as the parental strain for genomic modifications. Iterative rounds of A-Red recombineering (Jensen et al., loc. cit.) or P1 phage transduction (Thomason et al., Curr. Protoc. Mol. Biol. Chapter 1, Unit 1 17 (2007)) were used for gene deletions. For the recombineering, selectable resistance cassettes were generated via PCR—primers 50 bp homologous arms as in Baba et al. (Mol. Syst. Biol. 2 (2006), 2008-2008)—using the FRT-PGK-gb2-neo-FRT (Km) cassette (Gene Bridges, Germany) for kanamycin resistance (Km) and the pKD3 plasmid (GenBank: AY048742; Datsenko and Wanner, Proc. Natl. Acad. Sci. USA 97 (2000), 6640-6645) as template for chloramphenicol resistance cassettes (CAP). The procedures of the deletion, verification and antibiotic cassette removal are detailed in Wenk et al. (Methods Enzymol. 608 (2018), 329-367).

A similar strategy was applied to exchange the genomic promoter of target genes. A constitutive strong promoter pgi-20 (Brastsch St al., Biotechniques 45 (2008), 335-337) and a ribosome binding site "C" (AAGTTAAGAGGCAAGA (SEQ ID NO: 44); Zelcbuch et al., Nucleic Acids Res. 41 (2013), e98.) were constructed downstream of the CAP cassette using primers listed shown in Table 2.

TABLE 2

LIST OF OLIGO PRIMERS USED IN THIS STUDY

| PRIMER | SEQUENCE (5'→3') |
| --- | --- |
| RHMA_F | ATGCATCATCACCATCACCACAACGCATTATTAAGCAATCCC (SEQ ID NO: 6) |
| RHMA_R | GCGCTAGCTCAATAACTACCTTTTATGC (SEQ ID NO: 7) |
| YAGE_F | ATGCATCATCACCATCACCACACCGCAGTCCGCGTTGTTC (SEQ ID NO: 8) |
| YAGE_R | GCTAGCATTACCAAAGCTTGAGCTGTTG (SEQ ID NO: 9) |
| YJHH_F | ATGCATCATCACCATCACCACAAAAAAATTCAGCGGCATTATTCC (SEQ ID NO: 10) |
| YJHH_R | GCTAGCATTAGACTGGTAAAATGCCCT (SEQ ID NO: 11) |
| YJHH_C | TAATAAAGGGGTTGACGGGCTG (SEQ ID NO: 12) |
| YJHH_D | CAGCCCGTCAACCCCTTTATTA (SEQ ID NO: 13) |
| YJHH_A | GTAACCATTGTTGACGGGCGAG (SEQ ID NO: 14) |
| YJHH_B | CTCGCCCGTCAACAATGGTTAC (SEQ ID NO: 15) |
| DGOA_F | ATGCATCATCACCATCACCACACAGTGGCAAACTAAACTCC (SEQ ID NO: 16) |
| DGOA_R | GCTAGCATCATTGCACTGCCTCTCG (SEQ ID NO: 17) |
| DGOA_B | TCCCGCTGAACTCCCCACAATG (SEQ ID NO: 18) |
| DGOA_C | CATTGTGGGGAGTTCAGCGGGA (SEQ ID NO: 19) |
| EDA_A | GAATGCATCATCACCATCACCACAAAAACTGGAAAACAAGTGCAGAATCAATCCTGACCAC (SEQ ID NO: 20) |
| EDA_B | GAACGGACCCGCAATCGCTTGCAGGGCTTTCAC (SEQ ID NO: 21) |
| EDA_C | GTGAAAGCCCTGCAAGCGATTGCGGGTCCGTTC (SEQ ID NO: 22) |
| EDA_D | CGCTAGCTCTAGATTACAGCTTAGCGCCTTCTACAGCTTCACG (SEQ ID NO: 23) |
| MHPE_F | ATGCATCATCACCATCACCACAAACGGTAAAAAACTTTATATCTCGGACG (SEQ ID NO: 24) |
| MHPE_R | GCTAGCATTATTTGTTGTTGCGCAGATC (SEQ ID NO: 25) |
| LTAE_F | ATGCATCATCACCATCACCACATTGATTTACGCAGTGATACCGTTACCCGACC (SEQ ID NO: 26) |
| LTAE_B | GCTGCGTAGTCTTGCAGAGCATTAAC (SEQ ID NO: 27) |
| LTAE_C | GTTAATGCTCTGCAAGACTACGCAGC (SEQ ID NO: 28) |
| LTAE_R | CTCTTACGTGCCCGATCAACGCTAGCTTAACGCGCCAGGAATGCACGCCAG (SEQ ID NO: 29) |
| GARL_F | GTTAAGAGGCAAGAATGCATAATAACGATGTTTTCCCGAA (SEQ ID NO: 30) |
| GARL_R | CCGCGCTAGCTCTAGATTATTTTTTAAAGGTATCAGCCAGT (SEQ ID NO: 31) |
| ALAC_F | ATGCATCATCACCATCACCACGCTGACACTCGCCCTGAA (SEQ ID NO: 32) |
| ALAC_C | GCGCGGTGATTCCAGGGGCGCAGGTA (SEQ ID NO: 33) |
| ALAC_B | TACCTGCGCCCCTGGAATCACCGCGC (SEQ ID NO: 34) |
| ALAC_E | GCTATCACGATGACGGCACCTTTACG (SEQ ID NO: 35) |
| ALAC_D | CGTAAAGGTGCCGTCATCGTGATAGC (SEQ ID NO: 36) |
| ALAC_R | GCTAGCTTATTCCGCGTTTTCGTGAA (SEQ ID NO: 37) |
| PALAC_R | AGTAAACCGTCGGCACGGAACATC (SEQ ID NO: 38) |
| PALAC_F | CTCTATGATAGGTAACCTGAAGGCTGATGACCAGCAGGCCGTTTTTGAGGAATTAACCCTCACTAAAGGGCG (SEQ ID NO: 39) |
| PTHRBC_R | AACCCGACGCTCATATTGGCACTGGAAGCCGGGGCATAAACTTTAACCATTCTTGCCTCTTAACTTTAAAG (SEQ ID NO: 40) |

TABLE 2-continued

LIST OF OLIGO PRIMERS USED IN THIS STUDY

| PRIMER | SEQUENCE (5'→3') |
|---|---|
| PTHRBC_F | CAATGTTGCACCGTTTGCTGCATGATATTGAAAAAAATATCACCAAATAAAATTAACCCTCACT AAAGGGCG (SEQ ID NO: 41) |
| PASPC_F | GGTCCTGTTTTTTTTATACCTTCCAGAGCAATCTCACGTCTTGCAAAAACAATTAACCCTCACT AAAGGGCG (SEQ ID NO: 42) |
| PASPC_R | GCCAGGCCCAGAATCGGGTCGGCAGGAGCGGCGGTAATGTTCTCAAACATTCTTGCCTCTTAAC TTTAAAG (SEQ ID NO: 43) |

The synthetic promoter was first introduced to the SIJ488 strain by the recombineering method; P1 transduction was then used to transfer the synthetic promoter into the selection strains. thrB (encoding homoserine kinase, HSK) and thrC (encoding threonine synthase, TS) are on the same operon with thrL and thrA. Since thrL encodes a regulatory peptide and thrA is redundant in the Δasd selection strains, thrLA was deleted during the promoter exchange of thrBC. The point mutations A142P Y2750 (Bouzon et al., ACS Synthetic Biology 6 (2017), 1520-1533) were introduced along with the promoter exchange of alaC (In this case, the recombineering cassette has the mutated gene downstream the CAP cassette and synthetic promoter). Promoter exchanges were confirmed by sequencing the promoter regions.

Plasmids construction. All cloning procedures were carried out in E. coli DH5α strain. E. coli native genes ltaE, rhmA, garL, yagE, yjhH, eda, dgoA and mhpE, were cloned from E. coli MG1655 genome with the primers shown in Table 2, above.

NAD-dependent methanol dehydrogenase (CgAdhA) was taken from Corynebacterium glutamicum R after codon optimization (He et al., ACS Synthetic Biology 7 (2018), 1601-1611). Genes were inserted into a pNivC vector downstream of a ribosome binding site "C" (AAGTTAAGAGGCAAGA (SEQ ID NO: 44); Zelcbuch et al., Nucleic Acids Res. 41 (2013), e98.). The genes were assembled into one operon using BioBrick enzymes: BcuI, SalI, NheI and XhoI (FastDigest, Thermo Scientific; Zelcbuch et al., Nucleic Acids Res. 41 (2013), e98.). Using EcoRI and PstI, the synthetic operon was then inserted into an overexpression pZASS vector (Wenk et al., Methods Enzymol. 808 (2018), 329-387) under a constitutive strong promoter pgi-20 (Braatsch et al., Biotechniques 45 (2008), 335-337). The final plasmids are listed in the Table 3.

TABLE 3

SUPPLEMENTARY TABLE S4 THE LIST OF OVEREXPRESSION PLASMIDS

| PLASMID | GENES |
|---|---|
| PZASS | P15A ORI; STREP$^R$; P$_{PGI-20}$ |
| PZASS-MDH | PZASS::CGADHA |
| PZASS-LTAE-MDH | PZASS::LTAE, CGADHA |
| PZASS-LTAE | PZASS::LTAE |
| PZASS-MDH-RHMA | PZASS::CGADHA, RHMA |
| PZASS-RHMA | PZASS::RHMA |
| PZASS-MDH-GARL | PZASS::CGADHA, GARL |
| PZASS-GARL | PZASS::GARL |
| PZASS-MDH-YAGE | PZASS::CGADHA, YAGE |
| PZASS-YAGE | PZASS::YAGE |
| PZASS-MDH-YJHH | PZASS::CGADHA, YJHH |
| PZASS-YJHH | PZASS::YJHH |
| PZASS-MDH-EDA | PZASS::CGADHA, EDA |

TABLE 3-continued

SUPPLEMENTARY TABLE S4 THE LIST OF OVEREXPRESSION PLASMIDS

| PLASMID | GENES |
|---|---|
| PZASS-EDA | PZASS::EDA |
| PZASS-MDH-DGOA | PZASS::CGADHA, DGOA |
| PZASS-DGOA | PZASS::DGOA |
| PZASS-MDH-MHPE | PZASS::CGADHA, MHPE |
| PZASS-MHPE | PZASS::MHPE |

Growth media. LB medium (0.5% yeast extract, 1% tryptone, 1% NaCl) was used for strain engineering and recombinant plasmids cloning. Antibiotics were used at the following concentrations: kanamycin, 50 μg/mL; ampicillin, 100 μg/mL; streptomycin, 100 μg/mL; chloramphenicol, 30 μg/mL Growth experiments were performed in M9 minimal media (47.8 mM $Na_2HPO_4$, 22 mM $KH_2PO_4$, 8.6 mM NaCl, 18.7 mM $NH_4Cl$, 2 mM $MgSO_4$ and 100 μM $CaCl_2$), supplemented with trace elements (134 μM EDTA, 31 μM $FeCl_3$, 6.2 μM $ZnCl_2$, 0.76 μM $CuCl_2$, 0.42 μM $CoCl_2$, 1.62 μM $H_3BO_3$, 0.081 μM $MnCl_2$). Additional 50 μM $MnCl_2$ was added for all experiments since it improves in vivo activity of LtaE (FIG. 3). Carbon sources were added according to the strain and the specific experiment 10 mM glucose, 10 mM glycine, 10 mM serine, 10 mM threonine, 2 mM homoserine, and 1 mM isoleucine. 0.25 mM diaminopimelate (DAP) was supplemented in all media used to cultivate the Δasd strain (Cardineau and Curtiss, J. Biol. Chem. 282 (1987), 3344-3353).

Growth experiments. Strains were precultured in 4 ml M9 medium with proper carbon sources and streptomycin. The precultures were harvested and washed three times in M9 medium, then inoculated in M9 media with suitable carbon sources, with a starting $OD_{600}$ of 0.02. 150 μL of culture were added to each well of 96-well microplates (Nunclon Delta Surface, Thermo Scientific). Further 50 μL mineral oil (Sigma-Aldrich) was added to each well to avoid evaporation (while enabling gas diffusion). The 96-well microplates were incubated at 37° C. in microplate reader (BioTek EPOCH 2). The shaking program cycle (controlled by Gen5 v3) had 4 shaking phases, lasting 60 seconds each: linear shaking followed by orbital shaking, both at an amplitude of 3 mm, then linear shaking followed by orbital shaking both at an amplitude of 2 mm. The absorbance ($OD_{600}$) in each well was monitored and recorded after every three shaking cycles (~16.5 min). Raw data from the plate reader were calibrated to normal cuvette measured $OD_{600}$ values according to $OD_{cuvette} = OD_{plate}/0.23$. Growth parameters were calculated using MATLAB (MathWarks) based on three technical triplicates—the average values were used to generate the growth curves. Checked in MATLAB, in all cases variability between triplicate measurements were less than 5%.

Stable isotopic labelling. $^{13}C$-Methanol, glucose-1-$^{13}C$, glucose-2-$^{13}C$, glucose-3-$^{13}C$ were purchased from Sigma-Aldrich. Cells were harvested at the late exponential phase. The equivalent volume of 1 mL of culture at $OD_{600}$ of 1 was harvested and washed by centrifugation. Protein biomass was hydrolyzed with 6 M HCl, at 95° C. for 24 h (You et al., Journal of Visualized Experiments 59 (2012)). The samples were completely dried under a stream of air at WC. Hydrolyzed amino acids were analyzed with UPLC-ESI-MS as previously described (Giavalisco et al., Plant J. 68 (2011), 364-376). Chromatography was performed with a Waters Acquity UPLC system (Waters), using an HSS T3 $C_{18}$ reversed phase column (100 mm×2.1 mm, 1.8 µm; Waters). 0.1% formic acid in $H_2O$ (A) and 0.1% formic acid in acetonitrile (B) were the mobile phases. The flow rate was 0.4 mL/min and the gradient was: 0 to 1 min—99% A; 1 to 5 min—linear gradient from 99% A to 82%; 5 to 6 min—linear gradient from 82% A to 1% A; 6 to 8 min—kept at 1% A; 8-8.5 min—near gradient to 99% A 8.5-11 min—re-equilibrate. Mass spectra were acquired using an Exactive mass spectrometer (Thermo Scientific) in positive ionization mode, with a scan range of 50.0 to 300.0 m/z. The spectra were recorded during the first 5 min of the LC gradients. Data analysis was performed using Xcalibur (Thermo Scientific). The identification amino acids was based on retention times and m/z, which were determined by analyzing amino acid standards (Sigma-Aldrich) under the same conditions.

Molecular phylogenetic analysis. The protein sequences of the aldolases used to catalyze the HAL reaction were obtained from UniProt RhmA/YfaU P76469, GarL P23522, YagE P75682 and YjhH P39359, Eda P0A955, DgoA 06BF16 and MhpE P51020. MAFFT v7 (Katoh and Standley, Mol. Biol. Evol. 30 (2013), 772-780) was used for multiple sequence alignment with default parameters. The aligned sequences were used by MEGA X (Kumar et al., Mol. Biol. Evol. 35 (2018), 1547-1549) with Maximum Likelihood method to construct a phylogenetic tree. The bootstrap consensus tree was generated with the setting No. of bootstrap replications to 1000.

Example 1

Concept of the Newly Developed "Homoserine Cycle"

With the aim to provide a metabolic route which is superior to the known native serine cycle, a metabolic pathway was designed which is also referred herein as the "homoserine cycle". A representative example of the homoserine cycle is shown in FIG. 1.

In the homoserine cycle, glycine is directly condensed with formaldehyde to generate serine. This reaction (Item (6) in FIG. 1) (herein also referred to as the serine aldolase (SAL) reaction) was previously found to be promiscuously catalyzed (in vivo) by a threonine aldolase (LtaE) (Contestabile et al., Eur. J. Biochem. 268 (2001), 6508-6525). The SAL reaction bypasses the very long, multi-cofactor-dependent, and ATP-inefficient route for formaldehyde assimilation to 5,10-methylene-tetrahydrofolate ($CH_2$-THF) (Crowther et al., J. Bacteriol. 190 (2008), 5057-5062). As within the previously proposed modified serine cycles (Yu and Lao, Nature Communications 9 (2018), 3992; Bar-Even, Biochemistry 55 (2016), 3851-383), serine is then deaminated to pyruvate by serine deaminase (item (7) in FIG. 1), bypassing a longer route vim glycerate, which further involves the highly toxic intermediate hydroxypyruvate (Kim and Copley, Proc. Natl. Acad. Sci. USA 109 (2012), E2856-2864). Pyruvate is then condensed with formaldehyde to generate the non-natural metabolite 4-hydroxy-2-oxobutanoate (HOB) (Bouzon et al., ACS Synthetic Biology 6 (2017), 1520-1533), which is subsequently aminated to homoserine. The first of these reactions—(item (1) in FIG. 1)—was found to be promiscuously catalyzed by E. coli 2-keto-deoxy-L-rhamnonate aldolase (RhmA) (Hernandez et al., ACS Catal. 7 (2017), 1707-1711). The latter reaction—HOB amination (item (2) in FIG. 1)—is supported by numerous aminotransferases (Hernandez et al., ACS Catal. 7 (2017), 1707-1711; Walther et al., Metab. Eng. 45 (2018), 237-245; Zhong et al., ACS Synthetic Biology 8 (2019), 587-595) as well as amino acid dehydrogenases such as (engineered) glutamate dehydrogenase (Chen et al., Biotechnol. J. 10 (2015), 284-289). This route effectively replaces a carboxylation reaction (by phosphonopyruvate carboxylase) with a formaldehyde assimilation reaction that provides an alternative way to generate a $C_4$ intermediate. Homoserine is then converted into threonine, e.g. by the action of homoserine kinase (ThrB, item (3) in FIG. 1) and threonine synthase (ThrC, item (4) in FIG. 1). Finally, threonine is cleaved to produce glycine and acetaldehyde. This can, e.g., be achieved by making use of a threonine aldolase (item (5) in FIG. 1, for example by the same threonine aldolase (LtaE) that catalyzes the SAL reaction (item (6) in FIG. 1) to regenerate glycine and produce acetaldehyde. The produced acetaldehyde can, e.g., be further oxidized to acetyl-CoA and assimilated to central metabolism.

Demonstration of the In Vivo Activity of Enzymes Catalyzing the Condensation of Glycine and Formaldehyde into Serine As described above, several of the reactions of the newly proposed "homoserine cycle" correspond to the primary activities of their catalyzing enzymes and, thus, ae expected to be normally catalyzed in vivo by the respective enzymes and it is also expected that these reactions do not constrain pathway flux. However, three of the reactions of the newly designed "homoserine cycle" (i.e. items (1), (2) and (6) in FIG. 1), correspond to promiscuous activities that had so far only been characterized In vitro. Hence, for each of these promiscuous activities, it was tested whether they can also support the corresponding conversions in vivo. For this purpose, dedicated gene deletion strains were created, the growth of which is dependent on the activity of these reactions.

First, the ability of LtaE to catalyze the "SAL reaction" (item (6) in FIG. 1; FIG. 2a) in vivo was tested. Towards this aim two strains auxotrophic for glycine and serine were constructed. In both strains the gene encoding for 3-phosphoglycerate dehydrogenase (ΔserA) was deleted. In one strain the gene encoding serine hydroxymethyltransferase was also deleted (ΔglyA) while in the other strain the genes for the glycine cleavage system was deleted (ΔgcvTHP). The growth of these strains required the addition of both glycine and serine, as the cellular interconversion of these compounds is blocked (FIGS. 2b and c).

It was reasoned that if the SAL reaction indeed supports physiologically relevant flux, both strains should be able to grow when methanol dehydrogenase (MDH) and LtaE are overexpressed and serine is replaced with methanol in the medium. In the ΔserA ΔglyA strain, the SAL reaction would be responsible for the production of serine (FIG. 2b), which accounts for ~3% of the carbon in biomass (Neidhardt et al., in: Physiology of the Bacterial Cell: A Molecular Approach 134-143 (1990)). In the ΔserA ΔgcvTHP strain, the SAL reaction would be responsible for the production of both serine and the cellular $C_1$ moieties (FIG. 2c), together accounting for ~6% of the carbon in biomass (Neidhardt et al., loc. cit.). To avoid formaldehyde oxidation to formate, which might deplete its intracellular pool and constrain its assimilation, the genes encoding for the glutathione-dependent formaldehyde oxidation system were also deleted (ΔfrmRAB) (He et al., ACS Synthetic Biology 7 (2018), 1601-1611).

Upon overexpression of MDH and LtaE growth of both selection strains was observed with glucose as the main carbon source and glycine and methanol as precursors of sine (FIG. 2d,e). This indicates that the SAL reaction can operate in vivo at a physiologically significant rate. Expression of only MDH or only LtaE failed to sustain growth, indicating that the native expression of genomic ltaE is too low to support the SAL reaction. The observed growth rate and yield were dependent on the concentration of methanol, where the ΔserA ΔglyA ΔfrmRAB strain supported higher rates and yields than the ΔserA ΔgcvTHP ΔfrmRAB strain on low methanol concentrations. This corresponds to the prediction that the latter strain depends on the SAL reaction to provide a higher fraction of the cellular carbons. Methanol concentrations in the range of 200-1000 mM seem to be optimal, supporting growth rates similar to that of the positive control (in which serine is added to the medium). In all experiments, 50 µM $MnCl_2$ were added, as $Mn^{2+}$ Is a known cofactor of LtaE (Fesko, Appl. Microbiol. Biotechnol. 100 (2016), 2579-2590). Without the additional supplementation of $MnCl_2$, we the reactions still occur, but lower growth rates and yields were observed (see FIG. 3).

To confirm the activity of the SAL reaction, $^{13}C$-labeling experiments were conducted. Both strains were cultivated with $^{13}C$-methanol as well as unlabeled glucose and glycine. In the ΔserA ΔglyA ΔfrmRAB strain serine was found to be entirely singly labeled as expected, while the other amino acids were unlabeled (FIG. 2f). As threonine and methionine are derived from oxaloacetate, and hence carry a carbon that originates from $CO_2$ (i.e., anaplerotic reactions), their lack of labeling indicates that formaldehyde oxidation to $CO_2$ is negligible, as expected by the deletion of frmRAB. In the ΔserA ΔgcvTHP ΔfrmRAB strain serine, methionine, and histidine were found to be entirely singly labeled (FIG. 2g). Unlike threonine, both methionine and histidine harbor a carbon derived from THF carrying a $C_1$ unit—methyl-THF in the case of methionine and formyl-THF in the case of histidine (Yishai et al., ACS Synthetic Biology 6(9) (2017), 1722-1731). The labeling of these amino acids thus indicates that all cellular $C_1$ moieties are derived from methanol. Overall, the labeling results confirm that the SAL reaction provides the sole source of serine in both strains and the sole source of $C_1$ moieties in the ΔserA ΔgcvTHP ΔfrmRAB strain.

Next, it was tested whether it is possible to omit glycine from the medium, such that it will be produced endogenously via LtaE-dependent threonine cleavage (FIG. 4a). Towards this aim, in both selection strains, the genes encoding for threonine dehydrogenase and 2-amino-3-ketobutyrate CoA-ligase (Δkbl-tdh) were deleted, thus blocking the LtaE-independent route of threonine degradation (FIG. 4a) (Yishai et al., ACS Synthetic Biology 6(9) (2017), 1722-1731). It was found that replacing glycine with threonine did not alter the growth of either selection strain (FIG. 4b, note that growth was still strictly dependent on methanol). To enable this growth, the overexpressed LtaE catalyzes two subsequent reactions, first cleaving threonine to glycine and acetaldehyde and then reacting glycine with formaldehyde to produce serine. Hence, LtaE can be regarded as a glycyl-transferase—transferring a glycine moiety from one small aldehyde (acetaldehyde) to another (formaldehyde).

Next, it was assessed whether it was also possible to omit threonine from the medium and rely on native threonine biosynthesis to provide this amino acid as a precursor for glycine and serine (FIG. 4a). Indeed, despite showing reduced growth rates, both selection strains were able to grow with only glucose (as main carbon source) and methanol without the addition of glycine or threonine (green lines in FIG. 4b). This indicates that half of the homoserine cycle is active: homoserine (generated natively from aspartate) is metabolized to threonine via homoserine kinase (HSK) and threonine synthase (TS), and LtaE then cleaves threonine to glycine (and acetaldehyde) and condenses glycine with formaldehyde to produce swine (FIG. 4a).

To confirm that, also in the absence of externally provided glycine or threonine, all cellular serine is produced from glycine condensation with formaldehyde, $^{13}C$-labeling experiments were conducted. The strains were cultured in the presence of labeled or unlabeled methanol as well as glucose labeled at different carbons (glucose-1-$^{13}C$, glucose-2-$^{13}C$, and glucose-3-$^{13}C$). While the labeling pattern of glycine changed according to the labeled carbon of glucose, cultivation with $^{13}C$-methanol always resulted in exactly one more labeled carbon in serine than in glycine (FIG. 4c). This unequivocally confirms the methanol-dependent production of serine from glycine when the latter compound is produced internally from homoserine metabolism.

Overall, the obtained results confirm the capability of LtaE to convert threonine to serine in vivo by releasing acetaldehyde and assimilating formaldehyde. The findings further confirm the physiologically significant activity of half of the homoserine cycle, where homoserine metabolism to glycine and swine provided all the biomass requirement of these amino acids as well as cellular $C_1$ moieties, together consisting 10% of the carbon in biomass (Neidhardt et al., in: Physiology of the Bacterial Call: A Molecular Approach 134-143 (1990)).

Demonstration of the In Vivo Activity of Enzymes Catalyzing the Condensation of Glycine and Pyruvate to Form HOB and of the Conversion of HOB into Homoserine After demonstrating methanol-dependent conversion of homoserine to serine, the aim was to demonstrate methanol-dependent conversion of pyruvate to homoserine. To select for the in vivo conversion of pyruvate to homoserine and threonine via HOB production and amination, a homoserine auxotroph strain was constructed: a deletion of the gene coding for aspartate-semialdehyde dehydrogenase (asd) resulted in a strain capable of growing only when homoserine and diaminopimelate (DAP) (Cardineau and Curtiss, J. Biol. Chem. 262 (1987), 3344-3353) were added to the medium. In this strain, homoserine is metabolized to methionine, threonine, and isoleucine, while DAP is metabolized to lysine and peptidoglycans. (It is noted that despite being formally reversible, homoserine dehydrogenase was not able to oxidize homoserine to aspartate-semialdehyde, the precursor of DAP, and hence the addition of the letter intermediate to the medium was required).

Figure 5:
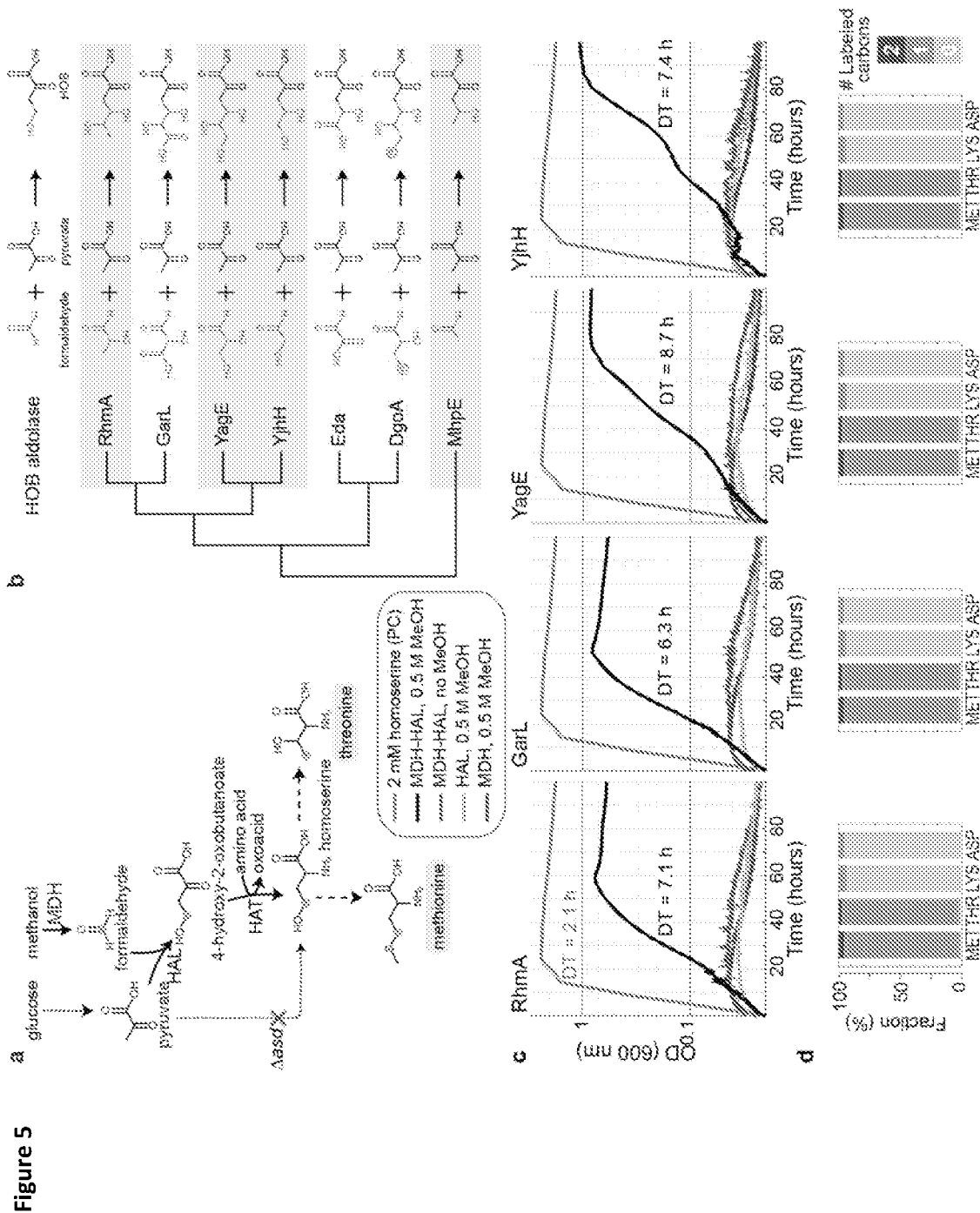

It was reasoned that, in the presence of methanol and methanol dehydrogenase, the combined activities of an enzyme catalyzing the formation of HOB by condensing pyruvate with formaldehyde and of an enzyme catalyzing the conversion of HOB into homoserine should enable the Δasd ΔfrmRAB strain to grow without the addition of homoserine to the medium (FIG. 5a). So far only RhmA was previously shown to catalyze the condensation of pyruvate with formaldehyde to produce HOB (Hernandez et al., ACS Catal. 7 (2017), 1707-1711). In order to find other enzymes which can catalyze this reaction, similar aldolases were tested for this activity. Hence, a search was conducted for all *E. coli* enzymes (strain MG1655, using EcoCyc; Keseler et al., Nucleic Acids Res. 33 (2005), D334-337) that are known to catalyze an aldolase reaction with pyruvate as an acceptor (and which might be able to use formaldehyde as a donor). Besides RhmA itself, six candidate aldolases were found: GarL, YagE, YjhH, Eda, DgoA, and MhpE (FIG. 5b). RhmA and GarL belong to the structural family of HpcH while mhpE belongs to DmpG family. Both of these families are Type II pyruvate aldolases which use a divalent metal cation for donor binding and enolization (Fang et al., Angew. Chem. Int. Ed. Engl. 58 (2019), 11841-11845). YagE and YjhH belong to the structural family of DHDPS while Ede and DgoA belong to KDPG family. These families are Type I pyruvate aldolases, using a lysine residue to form a Schiff base with the donor substrate (Fang et al., loc cit.).

It was found that overexpression of mdh together with rhmA, garL, yagE, or yjhH enabled growth of the Δasd ΔfrmRAB strain when homoserine was replaced with methanol (FIG. 5c). These four aldolase enzymes supported roughly the same growth rates. No growth was observed without methanol, or when methanol dehydrogenase or the aldolase enzymes were overexpressed alone. The relative sequence similarity between RhmA, GarL, YagE, and YjhH (FIG. 5b and FIG. 6 might explain why these enzymes, and not the others, were able to support the HAL reaction. Indeed, the structure of RhmA and GarL is almost identical (FIG. 7).

As the reaction converting HOB into homoserine is known to be supported by the native aspartate aminotransferase (AspC), a highly expressed protein (Li et al., Cell 157 (2014), 624635), and might be further catalyzed by other highly expressed, promiscuous aminotransferases, it was hypothesized that no dedicated enzyme overexpression would be required to enable this key reaction and this was indeed the case. In particular, growth was possible without dedicated overexpression of an aminotransferase enzyme. Genomic overexpression of aspC or of a mutated version of alanine aminotransferase (alaC*, the protein product of which was previously shown to catalyze the reaction in which homoserine is formed from HOB; Bouzon at al., ACS Synthetic Biology 6 (2017), 1520-1533) did not alter growth substantially (FIG. 8). Similarly, genomic overexpression of thrBC did not consistently assist growth (FIG. 8). This indicates that the reaction leading from HOB to homoserine, the homoserine kinase (HSK) reaction and the threonine synthase (TS) reaction do not constrain the flux from pyruvate to threonine.

To confirm that homoserine, and its downstream products threonine and methionine are produced from pyruvate and methanol via the reactions in which HOB is formed by the condensation of pyruvate with formaldehyde and the subsequent conversion of HOB into homoserine, $^{13}$C-labeling experiments we performed. Upon cultivation with unlabeled glucose and $^{13}$C-methanol, threonine and methionine were found to be completely once labeled, where lysine and aspartate (serving as control) were fully unlabeled. This confirms that homoserine and threonine are completely derived from pyruvate and methanol.

The invention claimed is:

1. A method for incorporation of formaldehyde into carbon compounds the can be assimilated into metabolism, said method comprising the following sequence of enzymatically catalyzed steps, wherein the method is carried out in vitro or in vivo:
   (1) condensation of pyruvate with a first formaldehyde into 4-hydroxy-2-oxobutanoic acid (HOB);
   (2) amination of the thus produced 4-hydroxy-2-oxobutanoic acid (HOB) to produce homoserine;
   (3) conversion of the thus produced homoserine to threonine;
   (4) conversion of the thus produced threonine into glycine and acetaldehyde or acetyl-CoA;
   (5) condensation of the thus produced glycine with a second formaldehyde to produce serine; and
   (6) conversion of the thus produced serine to produce pyruvate, wherein said pyruvate can then be used as a substrate in step (1);
   wherein the method comprises at least one of
   (a) in step (1) the condensation of pyruvate with formaldehyde into 4-hydroxy-2-oxobutanoic acid (HOB) is achieved using an aldolase classified in EC 4.1.2.;
   (b) in step (2) the amination of the 4-hydroxy-2-oxobutanoic acid (HOB) to produce homoserine is achieved by using an aminotransferase enzyme classified in EC 2.6.1. or by an amino acid dehydrogenase (EC 1.4.1._);
   (c) in step (3) the conversion of homoserine to threonine is achieved by (i) phosphorylation of the homoserine to produce o-phosphohomoserine achieved by using a homoserine kinase (EC 2.7.1.39); and (ii) dephosphorylation of the thus produced o-phosphohomoserine to produce threonine achieved by using a threonine synthase (EC 4.2.3.1);
   (d) in step (4) the conversion of the threonine into glycine and acetaldehyde is achieved by using a threonine aldolase (selected from the group consisting of EC 4.1.2.5, EC 4.1.2.6, EC 4.1.2.48 and EC 4.1.2.49) and/or the conversion of the threonine into glycine and acetyl-CoA is achieved by a combination of a threonine dehydrogenase (EC 1.1.1.103) and a 2-amino-3-ketobutyrate CoA ligase (EC 2.3.1.29);
   (e) in step (5) the condensation of the glycine with formaldehyde to produce serine is achieved by using a threonine aldolase selected from the group consisting of EC 4.1.2.5, EC 4.1.2.6, EC 4.1.2A8 and EC 4.1.2.49; and
   (f) in step (6) the conversion of the thus produced serine to produce pyruvate is achieved by using a serine deaminase (EC 4.3.1.17) or a threonine deaminase (EC4.3.1.19); or any combination of (a) to (f).

2. The method of claim 1, wherein the formaldehyde used for the condensation in step (1) and/or (5) is provided by the oxidation of methanol.

3. The method of claim 1, wherein the formaldehyde in step (1) and/or (5) is provided by
   (a) converting methanol enzymatically into formaldehyde using a methanol dehydrogenase (EC 1.1.1.244) or a methanol dehydrogenase (cytochrome c) (EC 1.1.2.7); and/or
   (b) converting methanol enzymatically into formaldehyde using an alcohol oxidase (EC 1.1.3.13).

* * * * *

SEQUENCE LISTING

<160> NUMBER OF SEQ ID NOS: 47

<210> SEQ ID NO 1
<211> LENGTH: 267
<212> TYPE: PRT
<213> ORGANISM: Escherichia coli
<220> FEATURE:
<223> OTHER INFORMATION: RhmA

<400> SEQUENCE: 1

```
Met Asn Ala Leu Leu Ser Asn Pro Phe Lys Glu Arg Leu Arg Lys Gly
1               5                   10                  15

Glu Val Gln Ile Gly Leu Trp Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140
```

-continued

```
Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
            165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
            195                 200                 205

Ala Gly Lys Ala Ala Gly Phe Leu Ala Val Ala Pro Asp Met Ala Gln
210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
            245                 250                 255

Gly Lys Asn Gly Pro Arg Ile Lys Gly Ser Tyr
            260                 265

<210> SEQ ID NO 2
<211> LENGTH: 302
<212> TYPE: PRT
<213> ORGANISM: Escherichia coli
<220> FEATURE:
<223> OTHER INFORMATION: YagE

<400> SEQUENCE: 2

Met Pro Gln Ser Ala Leu Phe Thr Gly Ile Ile Pro Pro Val Ser Thr
1               5                   10                  15

Ile Phe Thr Ala Asp Gly Gln Leu Asp Lys Pro Gly Thr Ala Ala Leu
            20                  25                  30

Ile Asp Asp Leu Ile Lys Ala Gly Val Asp Gly Leu Phe Phe Leu Gly
            35                  40                  45

Ser Gly Gly Glu Phe Ser Gln Leu Gly Ala Glu Glu Arg Lys Ala Ile
        50                  55                  60

Ala Arg Phe Ala Ile Asp His Val Asp Arg Arg Val Pro Val Leu Ile
65                  70                  75                  80

Gly Thr Gly Gly Thr Asn Ala Arg Glu Thr Ile Glu Leu Ser Gln His
            85                  90                  95

Ala Gln Gln Ala Gly Ala Asp Gly Ile Val Val Ile Asn Pro Tyr Tyr
            100                 105                 110

Trp Lys Val Ser Glu Ala Asn Leu Ile Arg Tyr Phe Glu Gln Val Ala
            115                 120                 125

Asp Ser Val Thr Leu Pro Val Met Leu Tyr Asn Phe Pro Ala Leu Thr
130                 135                 140

Gly Gln Asp Leu Thr Pro Ala Leu Val Lys Thr Leu Ala Asp Ser Arg
145                 150                 155                 160

Ser Asn Ile Ile Gly Ile Lys Asp Thr Ile Asp Ser Val Ala His Leu
            165                 170                 175

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
            195                 200                 205

Asp Gly Ala Ile Ser Ala Ser Gly Asn Phe Ala Pro Gln Val Ser Val
            210                 215                 220

Asn Leu Leu Lys Ala Trp Arg Asp Gly Asp Val Ala Lys Ala Ala Gly
225                 230                 235                 240
```

```
Tyr His Gln Thr Leu Leu Gln Ile Pro Gln Met Tyr Gln Leu Asp Thr
                245                 250                 255

Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
        275                 280                 285

Lys Ala Gln Leu Lys Thr Leu Leu Gln Gln Leu Lys Leu Cys
    290                 295                 300

<210> SEQ ID NO 3
<211> LENGTH: 301
<212> TYPE: PRT
<213> ORGANISM: Escherichia coli
<220> FEATURE:
<223> OTHER INFORMATION: YjhH

<400> SEQUENCE: 3

Met Lys Lys Phe Ser Gly Ile Ile Pro Pro Val Ser Ser Thr Phe His
1               5                   10                  15

Arg Asp Gly Thr Leu Asp Lys Lys Ala Met Arg Glu Val Ala Asp Phe
            20                  25                  30

Leu Ile Asn Lys Gly Val Asp Gly Leu Phe Tyr Leu Gly Thr Gly Gly
        35                  40                  45

Glu Phe Ser Gln Met Asn Thr Ala Gln Arg Met Ala Leu Ala Glu Glu
    50                  55                  60

Ala Val Thr Ile Val Asp Gly Arg Val Pro Val Leu Ile Gly Val Gly
65                  70                  75                  80

Ser Pro Ser Thr Asp Glu Ala Val Lys Leu Ala Gln His Ala Gln Ala
            85                  90                  95

Tyr Gly Ala Asp Gly Ile Val Ala Ile Asn Pro Tyr Tyr Trp Lys Val
            100                 105                 110

Ala Pro Arg Asn Leu Asp Asp Tyr Tyr Gln Gln Ile Ala Arg Ser Val
        115                 120                 125

Thr Leu Pro Val Ile Leu Tyr Asn Phe Pro Asp Leu Thr Gly Gln Asp
    130                 135                 140

Leu Thr Pro Glu Thr Val Thr Arg Leu Ala Leu Gln Asn Glu Asn Ile
145                 150                 155                 160

Val Gly Ile Lys Asp Thr Ile Asp Ser Val Gly His Leu Arg Thr Met
            165                 170                 175

Ile Asn Thr Val Lys Ser Val Arg Pro Ser Phe Ser Val Phe Cys Gly
        180                 185                 190

Tyr Asp Asp His Leu Leu Asn Thr Met Leu Leu Gly Gly Asp Gly Ala
    195                 200                 205

Ile Thr Ala Ser Ala Asn Phe Ala Pro Glu Leu Ser Val Gly Ile Tyr
    210                 215                 220

Arg Ala Trp Arg Glu Gly Asp Leu Ala Thr Ala Thr Leu Asn Lys
225                 230                 235                 240

Lys Leu Leu Gln Leu Pro Ala Ile Tyr Ala Leu Glu Thr Pro Phe Val
                245                 250                 255

Ser Leu Ile Lys Tyr Ser Met Gln Cys Val Gly Leu Pro Val Glu Thr
            260                 265                 270

Tyr Cys Leu Pro Pro Ile Leu Glu Ala Ser Glu Glu Ala Lys Asp Lys
        275                 280                 285

Val His Val Leu Leu Thr Ala Gln Gly Ile Leu Pro Val
    290                 295                 300
```

<210> SEQ ID NO 4
<211> LENGTH: 256
<212> TYPE: PRT
<213> ORGANISM: Escherichia coli
<220> FEATURE:
<223> OTHER INFORMATION: GarL

<400> SEQUENCE: 4

Met Asn Asn Asp Val Phe Pro Asn Lys Phe Lys Ala Ala Leu Ala Ala
1               5                   10                  15

Lys Gln Val Gln Ile Gly Cys Trp Ser Ala Leu Ser Asn Pro Ile Ser
            20                  25                  30

Thr Glu Val Leu Gly Leu Ala Gly Phe Asp Trp Leu Val Leu Asp Gly
        35                  40                  45

Glu His Ala Pro Asn Asp Ile Ser Thr Phe Ile Pro Gln Leu Met Ala
    50                  55                  60

Leu Lys Gly Ser Ala Ser Ala Pro Val Val Arg Val Pro Thr Asn Glu
65                  70                  75                  80

Pro Val Ile Ile Lys Arg Leu Leu Asp Ile Gly Phe Tyr Asn Phe Leu
                85                  90                  95

Ile Pro Phe Val Glu Thr Lys Glu Glu Ala Glu Leu Ala Val Ala Ser
            100                 105                 110

Thr Arg Tyr Pro Pro Glu Gly Ile Arg Gly Val Ser Val Ser His Arg
        115                 120                 125

Ala Asn Met Phe Gly Thr Val Ala Asp Tyr Phe Ala Gln Ser Asn Lys
    130                 135                 140

Asn Ile Thr Ile Leu Val Gln Ile Glu Ser Gln Gln Gly Val Asp Asn
145                 150                 155                 160

Val Asp Ala Ile Ala Ala Thr Glu Gly Val Asp Gly Ile Phe Val Gly
                165                 170                 175

Pro Ser Asp Leu Ala Ala Ala Leu Gly His Leu Gly Asn Ala Ser His
            180                 185                 190

Pro Asp Val Gln Lys Ala Ile Gln His Ile Phe Asn Arg Ala Ser Ala
        195                 200                 205

His Gly Lys Pro Ser Gly Ile Leu Ala Pro Val Glu Ala Asp Ala Arg
    210                 215                 220

Arg Tyr Leu Glu Trp Gly Ala Thr Phe Val Ala Val Gly Ser Asp Leu
225                 230                 235                 240

Gly Val Phe Arg Ser Ala Thr Gln Lys Leu Ala Asp Thr Phe Lys Lys
                245                 250                 255

<210> SEQ ID NO 5
<211> LENGTH: 333
<212> TYPE: PRT
<213> ORGANISM: Escherichia coli
<220> FEATURE:
<223> OTHER INFORMATION: LtaE

<400> SEQUENCE: 5

Met Ile Asp Leu Arg Ser Asp Thr Val Thr Arg Pro Ser Arg Ala Met
1               5                   10                  15

Leu Glu Ala Met Met Ala Ala Pro Val Gly Asp Asp Val Tyr Gly Asp
            20                  25                  30

Asp Pro Thr Val Asn Ala Leu Gln Asp Tyr Ala Ala Glu Leu Ser Gly
        35                  40                  45

Lys Glu Ala Ala Ile Phe Leu Pro Thr Gly Thr Gln Ala Asn Leu Val

```
          50                  55                  60
Ala Leu Leu Ser His Cys Glu Arg Gly Glu Tyr Ile Val Gly Gln
 65                  70                  75                  80

Ala Ala His Asn Tyr Leu Phe Glu Ala Gly Ala Ala Val Leu Gly
                 85                  90                  95

Ser Ile Gln Pro Gln Pro Ile Asp Ala Ala Asp Gly Thr Leu Pro
            100                 105                 110

Leu Asp Lys Val Ala Met Lys Ile Lys Pro Asp Asp Ile His Phe Ala
        115                 120                 125

Arg Thr Lys Leu Leu Ser Leu Glu Asn Thr His Asn Gly Lys Val Leu
        130                 135                 140

Pro Arg Glu Tyr Leu Lys Glu Ala Trp Glu Phe Thr Arg Glu Arg Asn
145                 150                 155                 160

Leu Ala Leu His Val Asp Gly Ala Arg Ile Phe Asn Ala Val Val Ala
                165                 170                 175

Tyr Gly Cys Glu Leu Lys Glu Ile Thr Gln Tyr Cys Asp Ser Phe Thr
            180                 185                 190

Ile Cys Leu Ser Lys Gly Leu Gly Thr Pro Val Gly Ser Leu Leu Val
        195                 200                 205

Gly Asn Arg Asp Tyr Ile Lys Arg Ala Ile Arg Trp Arg Lys Met Thr
210                 215                 220

Gly Gly Gly Met Arg Gln Ser Gly Ile Leu Ala Ala Ala Gly Ile Tyr
225                 230                 235                 240

Ala Leu Lys Asn Asn Val Ala Arg Leu Gln Glu Asp His Asp Asn Ala
                245                 250                 255

Ala Trp Met Ala Glu Gln Leu Arg Glu Ala Gly Ala Asp Val Met Arg
            260                 265                 270

Gln Asp Thr Asn Met Leu Phe Val Arg Val Gly Glu Asn Ala Ala
        275                 280                 285

Ala Leu Gly Glu Tyr Met Lys Ala Arg Asn Val Leu Ile Asn Ala Ser
        290                 295                 300

Pro Ile Val Arg Leu Val Thr His Leu Asp Val Ser Arg Glu Gln Leu
305                 310                 315                 320

Ala Glu Val Ala Ala His Trp Arg Ala Phe Leu Ala Arg
                325                 330

<210> SEQ ID NO 6
<211> LENGTH: 42
<212> TYPE: DNA
<213> ORGANISM: Artificial Sequence
<220> FEATURE:
<223> OTHER INFORMATION: Primer RHMA_F

<400> SEQUENCE: 6
atgcatcatc accatcacca caacgcatta ttaagcaatc cc                           42

<210> SEQ ID NO 7
<211> LENGTH: 28
<212> TYPE: DNA
<213> ORGANISM: Artificial Sequence
<220> FEATURE:
<223> OTHER INFORMATION: Primer RHMA_R

<400> SEQUENCE: 7
gcgctagctc aataactacc ttttatgc                                           28

<210> SEQ ID NO 8
```

<210> SEQ ID NO 8
<211> LENGTH: 40
<212> TYPE: DNA
<213> ORGANISM: Artificial Sequence
<220> FEATURE:
<223> OTHER INFORMATION: Primer YAGE_F

<400> SEQUENCE: 8
atgcatcatc accatcacca caccgcagtc cgcgttgttc          40

<210> SEQ ID NO 9
<211> LENGTH: 28
<212> TYPE: DNA
<213> ORGANISM: Artificial Sequence
<220> FEATURE:
<223> OTHER INFORMATION: Primer YAGE_R

<400> SEQUENCE: 9
gctagcatta gcaaagcttg agctgttg          28

<210> SEQ ID NO 10
<211> LENGTH: 45
<212> TYPE: DNA
<213> ORGANISM: Artificial Sequence
<220> FEATURE:
<223> OTHER INFORMATION: Primer YJHH_F

<400> SEQUENCE: 10
atgcatcatc accatcacca caaaaaaatt cagcggcatt attcc          45

<210> SEQ ID NO 11
<211> LENGTH: 27
<212> TYPE: DNA
<213> ORGANISM: Artificial Sequence
<220> FEATURE:
<223> OTHER INFORMATION: Primer YJHH_R

<400> SEQUENCE: 11
gctagcatta gactggtaaa atgccct          27

<210> SEQ ID NO 12
<211> LENGTH: 22
<212> TYPE: DNA
<213> ORGANISM: Artificial Sequence
<220> FEATURE:
<223> OTHER INFORMATION: Primer YJHH_C

<400> SEQUENCE: 12
taataaaggg gttgacgggc tg          22

<210> SEQ ID NO 13
<211> LENGTH: 22
<212> TYPE: DNA
<213> ORGANISM: Artificial Sequence
<220> FEATURE:
<223> OTHER INFORMATION: Primer YJHH_D

<400> SEQUENCE: 13
cagcccgtca acccctttat ta          22

<210> SEQ ID NO 14
<211> LENGTH: 22
<212> TYPE: DNA
<213> ORGANISM: Artificial Sequence
<220> FEATURE:
<223> OTHER INFORMATION: YJHH_A

<400> SEQUENCE: 14

-continued gtaaccattg ttgacgggcg ag                                            22

<210> SEQ ID NO 15
<211> LENGTH: 22
<212> TYPE: DNA
<213> ORGANISM: Artificial Sequence
<220> FEATURE:
<223> OTHER INFORMATION: Primer YJHH_B

<400> SEQUENCE: 15
ctcgcccgtc aacaatggtt ac                                            22

<210> SEQ ID NO 16
<211> LENGTH: 41
<212> TYPE: DNA
<213> ORGANISM: Artificial Sequence
<220> FEATURE:
<223> OTHER INFORMATION: Primer DGOA_F

<400> SEQUENCE: 16
atgcatcatc accatcacca cacagtggca aactaaactc c                       41

<210> SEQ ID NO 17
<211> LENGTH: 25
<212> TYPE: DNA
<213> ORGANISM: Artificial Sequence
<220> FEATURE:
<223> OTHER INFORMATION: Primer DGOA_R

<400> SEQUENCE: 17
gctagcatca ttgcactgcc tctcg                                         25

<210> SEQ ID NO 18
<211> LENGTH: 22
<212> TYPE: DNA
<213> ORGANISM: Artificial Sequence
<220> FEATURE:
<223> OTHER INFORMATION: Primer DGOA_B

<400> SEQUENCE: 18
tcccgctgaa ctccccacaa tg                                            22

<210> SEQ ID NO 19
<211> LENGTH: 22
<212> TYPE: DNA
<213> ORGANISM: Artificial Sequence
<220> FEATURE:
<223> OTHER INFORMATION: Primer DGOA_C

<400> SEQUENCE: 19
cattgtgggg agttcagcgg ga                                            22

<210> SEQ ID NO 20
<211> LENGTH: 61
<212> TYPE: DNA
<213> ORGANISM: Artificial Sequence
<220> FEATURE:
<223> OTHER INFORMATION: Primer EDA_A

<400> SEQUENCE: 20
gaatgcatca tcaccatcac cacaaaaact ggaaaacaag tgcagaatca atcctgacca   60
c                                                                   61

<210> SEQ ID NO 21

<211> LENGTH: 33
<212> TYPE: DNA
<213> ORGANISM: Artificial Sequence
<220> FEATURE:
<223> OTHER INFORMATION: Primer EDA_B

<400> SEQUENCE: 21
gaacggaccc gcaatcgctt gcagggcttt cac        33

<210> SEQ ID NO 22
<211> LENGTH: 33
<212> TYPE: DNA
<213> ORGANISM: Artificial Sequence
<220> FEATURE:
<223> OTHER INFORMATION: Primer EDA_C

<400> SEQUENCE: 22
gtgaaagccc tgcaagcgat tgcgggtccg ttc        33

<210> SEQ ID NO 23
<211> LENGTH: 43
<212> TYPE: DNA
<213> ORGANISM: Artificial Sequence
<220> FEATURE:
<223> OTHER INFORMATION: Primer EDA_D

<400> SEQUENCE: 23
cgctagctct agattacagc ttagcgcctt ctacagcttc acg        43

<210> SEQ ID NO 24
<211> LENGTH: 50
<212> TYPE: DNA
<213> ORGANISM: Artificial Sequence
<220> FEATURE:
<223> OTHER INFORMATION: Primer MHPE_F

<400> SEQUENCE: 24
atgcatcatc accatcacca caaacggtaa aaaactttat atctcggacg        50

<210> SEQ ID NO 25
<211> LENGTH: 28
<212> TYPE: DNA
<213> ORGANISM: Artificial Sequence
<220> FEATURE:
<223> OTHER INFORMATION: Primer MHPE_R

<400> SEQUENCE: 25
gctagcatta tttgttgttg cgcagatc        28

<210> SEQ ID NO 26
<211> LENGTH: 53
<212> TYPE: DNA
<213> ORGANISM: Artificial Sequence
<220> FEATURE:
<223> OTHER INFORMATION: Primer LTAE_F

<400> SEQUENCE: 26
atgcatcatc accatcacca cattgattta cgcagtgata ccgttacccg acc        53

<210> SEQ ID NO 27
<211> LENGTH: 26
<212> TYPE: DNA
<213> ORGANISM: Artificial Sequence
<220> FEATURE:
<223> OTHER INFORMATION: Primer LTAE_B

<400> SEQUENCE: 27
gctgcgtagt cttgcagagc attaac                                          26

<210> SEQ ID NO 28
<211> LENGTH: 26
<212> TYPE: DNA
<213> ORGANISM: Artificial Sequence
<220> FEATURE:
<223> OTHER INFORMATION: Primer LTAE_C

<400> SEQUENCE: 28
gttaatgctc tgcaagacta cgcagc                                          26

<210> SEQ ID NO 29
<211> LENGTH: 51
<212> TYPE: DNA
<213> ORGANISM: Artificial Sequence
<220> FEATURE:
<223> OTHER INFORMATION: Primer LTAE_R

<400> SEQUENCE: 29
ctcttacgtg cccgatcaac gctagcttaa cgcgccagga atgcacgcca g              51

<210> SEQ ID NO 30
<211> LENGTH: 40
<212> TYPE: DNA
<213> ORGANISM: Artificial Sequence
<220> FEATURE:
<223> OTHER INFORMATION: Primer GARL_F

<400> SEQUENCE: 30
gttaagaggc aagaatgcat aataacgatg ttttcccgaa                           40

<210> SEQ ID NO 31
<211> LENGTH: 41
<212> TYPE: DNA
<213> ORGANISM: Artificial Sequence
<220> FEATURE:
<223> OTHER INFORMATION: Primer GARL_R

<400> SEQUENCE: 31
ccgcgctagc tctagattat tttttaaagg tatcagccag t                         41

<210> SEQ ID NO 32
<211> LENGTH: 39
<212> TYPE: DNA
<213> ORGANISM: Artificial Sequence
<220> FEATURE:
<223> OTHER INFORMATION: Primer ALAC_F

<400> SEQUENCE: 32
atgcatcatc accatcacca cgctgacact cgccctgaa                            39

<210> SEQ ID NO 33
<211> LENGTH: 26
<212> TYPE: DNA
<213> ORGANISM: Artificial Sequence
<220> FEATURE:
<223> OTHER INFORMATION: Primer ALAC_C

<400> SEQUENCE: 33
gcgcggtgat tccaggggcg caggta                                          26

<210> SEQ ID NO 34
<211> LENGTH: 26
<212> TYPE: DNA

<213> ORGANISM: Artificial Sequence
<220> FEATURE:
<223> OTHER INFORMATION: Primer ALAC_B

<400> SEQUENCE: 34
tacctgcgcc cctggaatca ccgcgc                                          26

<210> SEQ ID NO 35
<211> LENGTH: 26
<212> TYPE: DNA
<213> ORGANISM: Artificial Sequence
<220> FEATURE:
<223> OTHER INFORMATION: Primer ALAC_E

<400> SEQUENCE: 35
gctatcacga tgacggcacc tttacg                                          26

<210> SEQ ID NO 36
<211> LENGTH: 26
<212> TYPE: DNA
<213> ORGANISM: Artificial Sequence
<220> FEATURE:
<223> OTHER INFORMATION: Primer ALAC_D

<400> SEQUENCE: 36
cgtaaaggtg ccgtcatcgt gatagc                                          26

<210> SEQ ID NO 37
<211> LENGTH: 26
<212> TYPE: DNA
<213> ORGANISM: Artificial Sequence
<220> FEATURE:
<223> OTHER INFORMATION: Primer ALAC_R

<400> SEQUENCE: 37
gctagcttat tccgcgtttt cgtgaa                                          26

<210> SEQ ID NO 38
<211> LENGTH: 24
<212> TYPE: DNA
<213> ORGANISM: Artificial Sequence
<220> FEATURE:
<223> OTHER INFORMATION: Primer PALAC_R

<400> SEQUENCE: 38
agtaaaccgt cggcacggaa catc                                            24

<210> SEQ ID NO 39
<211> LENGTH: 72
<212> TYPE: DNA
<213> ORGANISM: Artificial Sequence
<220> FEATURE:
<223> OTHER INFORMATION: Primer PALAC_F

<400> SEQUENCE: 39
ctctatgata ggtaacctga aggctgatga ccagcaggcc gtttttgagg aattaaccct     60
cactaaaggg cg                                                         72

<210> SEQ ID NO 40
<211> LENGTH: 71
<212> TYPE: DNA
<213> ORGANISM: Artificial Sequence
<220> FEATURE:
<223> OTHER INFORMATION: Primer PTHRBC_R

<400> SEQUENCE: 40

```
aacccgacgc tcatattggc actggaagcc ggggcataaa ctttaaccat tcttgcctct    60
taactttaaa g                                                         71
```

<210> SEQ ID NO 41
<211> LENGTH: 72
<212> TYPE: DNA
<213> ORGANISM: Artificial Sequence
<220> FEATURE:
<223> OTHER INFORMATION: Primer PTHRBC_F

<400> SEQUENCE: 41

```
caatgttgca ccgtttgctg catgatattg aaaaaaatat caccaaataa aattaaccct    60
cactaaaggg cg                                                        72
```

<210> SEQ ID NO 42
<211> LENGTH: 72
<212> TYPE: DNA
<213> ORGANISM: Artificial Sequence
<220> FEATURE:
<223> OTHER INFORMATION: Primer PASPC_F

<400> SEQUENCE: 42

```
ggtcctgttt ttttatacc ttccagagca atctcacgtc ttgcaaaaac aattaaccct     60
cactaaaggg cg                                                        72
```

<210> SEQ ID NO 43
<211> LENGTH: 71
<212> TYPE: DNA
<213> ORGANISM: Artificial Sequence
<220> FEATURE:
<223> OTHER INFORMATION: Primer PASPC_R

<400> SEQUENCE: 43

```
gccaggccca gaatcgggtc ggcaggagcg gcggtaatgt tctcaaacat tcttgcctct    60
taactttaaa g                                                         71
```

<210> SEQ ID NO 44
<211> LENGTH: 16
<212> TYPE: DNA
<213> ORGANISM: Artificial Sequence
<220> FEATURE:
<223> OTHER INFORMATION: Ribosome binding site

<400> SEQUENCE: 44

```
aagttaagag gcaaga                                                    16
```

<210> SEQ ID NO 45
<211> LENGTH: 213
<212> TYPE: PRT
<213> ORGANISM: Escherichia coli
<220> FEATURE:
<223> OTHER INFORMATION: EDA

<400> SEQUENCE: 45

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val

```
                 50                  55                  60
Pro Glu Ala Ile Val Gly Ala Gly Thr Val Leu Asn Pro Gln Gln Leu
 65                  70                  75                  80

Ala Glu Val Thr Glu Ala Gly Ala Gln Phe Ala Ile Ser Pro Gly Leu
                 85                  90                  95

Thr Glu Pro Leu Leu Lys Ala Ala Thr Glu Gly Thr Ile Pro Leu Ile
                100                 105                 110

Pro Gly Ile Ser Thr Val Ser Glu Leu Met Leu Gly Met Asp Tyr Gly
                115                 120                 125

Leu Lys Glu Phe Lys Phe Phe Pro Ala Glu Ala Asn Gly Gly Val Lys
            130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
                180                 185                 190

Glu Ala Gly Asp Tyr Asp Arg Ile Thr Lys Leu Ala Arg Glu Ala Val
                195                 200                 205

Glu Gly Ala Lys Leu
            210

<210> SEQ ID NO 46
<211> LENGTH: 205
<212> TYPE: PRT
<213> ORGANISM: Escherichia coli
<220> FEATURE:
<223> OTHER INFORMATION: dgoA

<400> SEQUENCE: 46

Met Gln Trp Gln Thr Lys Leu Pro Leu Ile Ala Ile Leu Arg Gly Ile
  1               5                  10                  15

Thr Pro Asp Glu Ala Leu Ala His Val Gly Ala Val Ile Asp Ala Gly
                 20                  25                  30

Phe Asp Ala Val Glu Ile Pro Leu Asn Ser Pro Gln Trp Glu Gln Ser
             35                  40                  45

Ile Pro Ala Ile Val Asp Ala Tyr Gly Asp Lys Ala Leu Ile Gly Ala
 50                  55                  60

Gly Thr Val Leu Lys Pro Glu Gln Val Asp Ala Leu Ala Arg Met Gly
 65                  70                  75                  80

Cys Gln Leu Ile Val Thr Pro Asn Ile His Ser Glu Val Ile Arg Arg
                 85                  90                  95

Ala Val Gly Tyr Gly Met Thr Val Cys Pro Gly Cys Ala Thr Ala Thr
                100                 105                 110

Glu Ala Phe Thr Ala Leu Glu Ala Gly Ala Gln Ala Leu Lys Ile Phe
            115                 120                 125

Pro Ser Ser Ala Phe Gly Pro Gln Tyr Ile Lys Ala Leu Lys Ala Val
            130                 135                 140

Leu Pro Ser Asp Ile Ala Val Phe Ala Val Gly Gly Val Thr Pro Glu
145                 150                 155                 160

Asn Leu Ala Gln Trp Ile Asp Ala Gly Cys Ala Gly Ala Gly Leu Gly
                165                 170                 175

Ser Asp Leu Tyr Arg Ala Gly Gln Ser Val Glu Arg Thr Ala Gln Gln
            180                 185                 190

Ala Ala Ala Phe Val Lys Ala Tyr Arg Glu Ala Val Gln
```

```
            195                 200                 205

<210> SEQ ID NO 47
<211> LENGTH: 337
<212> TYPE: PRT
<213> ORGANISM: Escherichia coli
<220> FEATURE:
<223> OTHER INFORMATION: mhpE

<400> SEQUENCE: 47

Met Asn Gly Lys Lys Leu Tyr Ile Ser Asp Val Thr Leu Arg Asp Gly
1               5                   10                  15

Met His Ala Ile Arg His Gln Tyr Ser Leu Glu Asn Val Arg Gln Ile
            20                  25                  30

Ala Lys Ala Leu Asp Asp Ala Arg Val Asp Ser Ile Glu Val Ala His
        35                  40                  45

Gly Asp Gly Leu Gln Gly Ser Ser Phe Asn Tyr Gly Phe Gly Ala His
    50                  55                  60

Ser Asp Leu Glu Trp Ile Glu Ala Ala Asp Val Val Lys His Ala
65                  70                  75                  80

Lys Ile Ala Thr Leu Leu Leu Pro Gly Ile Gly Thr Ile His Asp Leu
                85                  90                  95

Lys Asn Ala Trp Gln Ala Gly Ala Arg Val Val Arg Val Ala Thr His
            100                 105                 110

Cys Thr Glu Ala Asp Val Ser Ala Gln His Ile Gln Tyr Ala Arg Glu
        115                 120                 125

Leu Gly Met Asp Thr Val Gly Phe Leu Met Met Ser His Met Thr Thr
    130                 135                 140

Pro Glu Asn Leu Ala Lys Gln Ala Lys Leu Met Glu Gly Tyr Gly Ala
145                 150                 155                 160

Thr Cys Ile Tyr Val Val Asp Ser Gly Gly Ala Met Asn Met Ser Asp
                165                 170                 175

Ile Arg Asp Arg Phe Arg Ala Leu Lys Ala Glu Leu Lys Pro Glu Thr
            180                 185                 190

Gln Thr Gly Met His Ala His His Asn Leu Ser Leu Gly Val Ala Asn
        195                 200                 205

Ser Ile Ala Ala Val Glu Glu Gly Cys Asp Arg Ile Asp Ala Ser Leu
    210                 215                 220

Ala Gly Met Gly Ala Gly Ala Gly Asn Ala Pro Leu Glu Val Phe Ile
225                 230                 235                 240

Ala Ala Ala Asp Lys Leu Gly Trp Gln His Gly Thr Asp Leu Tyr Ala
                245                 250                 255

Leu Met Asp Ala Ala Asp Asp Leu Val Arg Pro Leu Gln Asp Arg Pro
            260                 265                 270

Val Arg Val Asp Arg Glu Thr Leu Ala Leu Gly Tyr Ala Gly Val Tyr
        275                 280                 285

Ser Ser Phe Leu Arg His Cys Glu Thr Ala Ala Arg Tyr Gly Leu
    290                 295                 300

Ser Ala Val Asp Ile Leu Val Glu Leu Gly Lys Arg Arg Met Val Gly
305                 310                 315                 320

Gly Gln Glu Asp Met Ile Val Asp Val Ala Leu Asp Leu Arg Asn Asn
                325                 330                 335

Lys
```